US009534954B2

(12) United States Patent
Matsuno et al.

(10) Patent No.: US 9,534,954 B2
(45) Date of Patent: Jan. 3, 2017

(54) OPTICAL FILTER DEVICE, OPTICAL MODULE, AND ELECTRONIC APPARATUS

(71) Applicant: Seiko Epson Corporation, Tokyo (JP)

(72) Inventors: Yasushi Matsuno, Matsumoto (JP); Shuichi Tanaka, Chino (JP); Akira Sano, Shiojiri (JP)

(73) Assignee: Seiko Epson Corporation (JP)

( * ) Notice: Subject to any disclaimer, the term of this patent is extended or adjusted under 35 U.S.C. 154(b) by 1066 days.

(21) Appl. No.: 13/627,556

(22) Filed: Sep. 26, 2012

(65) Prior Publication Data
US 2013/0075596 A1 Mar. 28, 2013

(30) Foreign Application Priority Data

Sep. 27, 2011 (JP) ................. 2011-211497

(51) Int. Cl.
G01J 3/26 (2006.01)
G01J 3/51 (2006.01)
G01N 21/31 (2006.01)
G02B 26/00 (2006.01)

(52) U.S. Cl.
CPC .. *G01J 3/26* (2013.01); *G01J 3/51* (2013.01); *G02B 26/001* (2013.01); *G01N 21/31* (2013.01)

(58) Field of Classification Search
CPC ....... G02B 6/29358; G02B 26/001; G01J 3/26
USPC .................. 359/260, 577–590; 356/450–521
See application file for complete search history.

(56) References Cited

U.S. PATENT DOCUMENTS

| 4,609,566 | A | 9/1986 | Hongo et al. |
| 6,888,656 | B2 | 5/2005 | Miyajima et al. |
| 6,985,281 | B2 | 1/2006 | Wagner et al. |
| 7,002,697 | B2 | 2/2006 | Domash et al. |
| 7,514,685 | B2 | 4/2009 | Yoshida |
| 7,744,220 | B2 | 6/2010 | Masunishi et al. |
| 2006/0183644 | A1 | 8/2006 | Nakamura et al. |
| 2007/0241451 | A1 | 10/2007 | Koizumi et al. |
| 2008/0062426 | A1 | 3/2008 | Yoshida |

(Continued)

FOREIGN PATENT DOCUMENTS

| EP | 0 773 435 | 5/1997 |
| JP | 02-012218 | 1/1990 |

(Continued)

OTHER PUBLICATIONS

Extended European Search Report Issued in Counterpart European Application 12185857.5 dated Jan. 31, 2013.

*Primary Examiner* — Kimberly N Kakalec
(74) *Attorney, Agent, or Firm* — Harness, Dickey & Pierce, P.L.C.

(57) ABSTRACT

An optical filter device includes a variable wavelength interference filter having a stationary substrate, a movable substrate, a stationary reflecting film, and a movable reflecting film, and a housing adapted to house the variable wavelength interference filter therein. The housing has a base substrate, a lid bonded to the base substrate, and forming an internal space between the base substrate and the lid, and a lid-side glass substrate adapted to block a light passage hole provided to the lid. Further, the lid-side glass substrate has a substrate edge located outside the outer peripheral edge of the light passage hole, and is bonded to the lid in an area extending from the outer peripheral edge of the light passage hole to the substrate edge.

18 Claims, 13 Drawing Sheets

(56) References Cited

U.S. PATENT DOCUMENTS

| | | | |
|---|---|---|---|
| 2008/0079141 A1* | 4/2008 | Tien | B81B 7/0064 |
| | | | 257/704 |
| 2009/0309203 A1* | 12/2009 | Seppala | B81B 7/0038 |
| | | | 257/682 |
| 2010/0302660 A1 | 12/2010 | Hirokubo et al. | |
| 2011/0019202 A1 | 1/2011 | Iwaki et al. | |
| 2012/0154915 A1 | 6/2012 | Hiokubo | |

FOREIGN PATENT DOCUMENTS

| | | |
|---|---|---|
| JP | 2002-214561 | 7/2002 |
| JP | 2005-510756 | 4/2005 |
| JP | 2007-287967 A | 11/2007 |
| JP | 2008-070163 | 3/2008 |
| JP | 2008-076749 A | 4/2008 |
| JP | 2009-042458 | 2/2009 |
| JP | 2011-008225 | 1/2011 |
| JP | 2011-027780 A | 2/2011 |
| JP | 2012-168362 | 9/2012 |

* cited by examiner

001
OPTICAL FILTER DEVICE, OPTICAL MODULE, AND ELECTRONIC APPARATUS

BACKGROUND

1. Technical Field

The present invention relates to an optical filter device, an optical module, and an electronic apparatus.

2. Related Art

In the past, there has been known an interference filter having reflecting films respectively disposed on surfaces of a pair of substrates so as to be opposed to each other across a predetermined gap, the surfaces being opposed to each other. Further, there is known an optical filter device having such an interference filter housed in a housing (see, e.g., JP-A-2008-70163).

The optical filter device described in JP-A-2008-70163 is provided with a package (a housing) having a plate-like pedestal and a cylindrical cap. The housing has a peripheral edge portion of the pedestal and one end portion of the cylinder of the cap connected to each other by welding or bonding, and a space for housing the interference filter is disposed between the pedestal and the cap. Further, the cap is provided with a hole disposed on the upper surface opposed to the pedestal, and the hole is provided with a window section for allowing light to pass therethrough.

Although JP-A-2008-70163 discloses (e.g., FIG. 6) the configuration in which the window section is fitted in the hole in the upper surface of the cap regarding the method of providing the window section, it fails to disclose other specific configurations. In the configuration disclosed in FIG. 6 of JP-A-2008-70163, there is a problem that it is not possible to sufficiently assure the airtightness of the seal between the window section and the hole. Thus, for example, if the inside of the package is desired to be kept at a reduced-pressure, air may enter the inside through a gap between the window section and the hole to thereby make it impossible to maintain the reduced-pressure state. Further, the probability that foreign matter such as electrically-charged particles or water particles enter the inside through, for example, the gap between the window section and the hole is also raised.

SUMMARY

An advantage of some aspects of the invention is to provide an optical filter device, an optical module, and an electronic apparatus capable of keeping the inside airtightness preferable.

An optical filter device according to one aspect of the invention includes an interference filter having a first substrate, a second substrate opposed to the first substrate, a first reflecting film provided to the first substrate, and a second reflecting film provided to the second substrate and opposed to the first reflecting film across an inter-reflecting film gap, and a housing adapted to house the interference filter, the housing is provided with a base substrate, and a lid bonded to the base substrate, and forming an internal space capable of housing the interference filter between the lid and the base substrate, at least one of the base substrate and the lid is provided with a light passage hole in an area opposed to the first reflecting film and the second reflecting film, the housing has a light transmissive substrate adapted to cover the light passage hole, a substrate edge of the light transmissive substrate is located outside an outer peripheral edge of the light passage hole in a plan view of the light transmissive substrate viewed from a thickness direction of the light transmissive substrate, and the light transmissive substrate is bonded to at least the one of the base substrate and the lid provided with the light passage hole in an area extending from the outer peripheral edge of the light passage hole to the substrate edge in the plan view.

According to this aspect of the invention, the optical filter device is provided with the interference filter, and the housing for housing the interference filter. Further, the housing is provided with the base substrate and the lid, and by bonding the base substrate and the lid to each other, the internal space for housing the variable wavelength interference filter is formed.

Further, at least one of the base substrate and the lid is provided with the light passage hole for passing the light to the interference filter. Here, if the interference filter is a reflective filter for reflecting the light emitted due to the multiple interferences toward the light entrance side, it is possible to provide the light passage hole to either one of the base substrate and the lid. In contrast, if the interference filter is a transmissive filter for transmitting the light emitted due to the multiple interferences toward the side opposite to the light entrance side, the light passage hole is provided to each of the base substrate and the lid.

Further, in this aspect of the invention, the airtightness of the internal space is maintained by the light transmissive substrate covering the light passage hole. Here, the light transmissive substrate is formed to be larger than the light passage hole, and the area of the light transmissive substrate from the substrate edge thereof to the outer peripheral edge of the light passage hole is bonded to the base substrate or the lid provided with the light passage hole. In other words, in some aspects of the invention, the expression "the light transmissive substrate covers the light passage hole" denotes the state in which the light transmissive substrate is disposed so as to overlap (cover) the light passage hole in the plan view described above, and at the same time the periphery of the light passage hole has contact with the light transmissive substrate. Therefore, no gap occurs between the light transmissive substrate and the light passage hole, and the airtightness of the internal space is surely achieved.

According to this configuration, the bonding area of the light transmissive substrate increases, and a gap is reliably prevented, and thus it is possible to preferably keep the airtightness of the inside of the optical filter device compared to the configuration of, for example, fitting the light transmissive substrate into the light passage hole. Therefore, it is possible to surely prevent water particles and electrically-charged particles from entering the inside of the housing. Thus, it is possible to prevent the problem that, for example, the first reflecting film and the second reflecting film are deteriorated due to the water particles, and the problem that the first reflecting film and the second reflecting film are charged by the electrically-charged particles thereby varying the inter-reflecting film gap due to the Coulomb force.

In the optical filter device according to the above aspect of the invention, it is preferable that the lid includes a lid bonding section to be bonded to the base substrate, a sidewall section continuous to the lid bonding section, and rising in a direction intersecting with the base substrate, and a top surface section opposed to the base substrate and continuous to the sidewall section.

In this configuration, the lid bonding section of the lid is bonded to the base substrate, and there is provided the sidewall section continuous to the lid bonding section and rising in a direction intersecting with the substrate surface of the base substrate. In other words, the sidewall section extends from the lid bonding section in the direction extending away from the base substrate. Further, the top surface section is continuously disposed to the sidewall section so as to be opposed to the base substrate. According to such a configuration as described above, by bonding the lid to the base substrate, the internal space can be formed by the sidewall section and the top surface section of the lid, and the base substrate.

In the optical filter device according to the above aspect of the invention, it is preferable that the light transmissive substrate is bonded to an exterior surface of the one of the base substrate and the lid provided with the light passage hole, the exterior surface being opposite to the surface facing the interference filter.

In the case in which the light transmissive substrate is bonded to the internal space side, it results that the volume of the internal space is reduced in accordance with the thickness dimension of the light transmissive substrate, and the arrangement space for the interference filter is limited. In this case, in order to provide the arrangement space for the interference filter, it is desired to increase the size of the housing in some cases. In contrast, according to the configuration described above, the light transmissive substrate is bonded to the exterior surface side of the base substrate or the lid, which is the opposite side to the internal space. Therefore, the sufficient space volume of the internal space can be provided, and downsizing of the housing can be achieved.

In the optical filter device according to the above aspect of the invention, it is preferable that the light passage hole is provided to each of the base substrate and the lid, and the light transmissive substrate is provided to each of the two light passage holes.

The configuration of this aspect of the invention can be applied particularly to the case in which the transmissive filter for transmitting the light emitted by the multiple interferences to the opposite side to the light entrance side is used as the interference filter. In such an optical filter device as described above, it is possible to emit the light, which has been transmitted through the interference filter, directly outside from the light passage hole.

Further, in the case of using the reflective filter, it is required that the detection section for detecting the light reflected toward the light entrance side is arranged on the light entrance side, and the problem that the incident light enters the detection section might occur. In contrast, according to the configuration of using the transmissive filter, and providing the light passage holes to both the base substrate and the lid as described above, the detection of the incident light in the detection section can be suppressed, and thus, a more accurate detection process can be performed.

In the optical filter device according to the above aspect of the invention, it is preferable that the pressure in the internal space is lower than atmospheric pressure.

According to this configuration, the pressure of the internal space is reduced. Therefore, in the case of adopting the configuration in which the inter-reflecting film gap can be changed by, for example, the interference filter deflecting either one of the first substrate and the second substrate, the air resistance when deflecting the substrate is reduced to thereby make the response preferable. Further, for example, even in the case of using the optical filter device in an environment with large temperature variation, deformation of the light transmissive substrate and deformation of the interference filter due to the increase in pressure of the internal space can be suppressed.

In the optical filter device according to the above aspect of the invention, it is preferable that in the plan view of the light transmissive substrate viewed from a thickness direction of the light transmissive substrate, denoting two intersections between a straight line connecting two points on an outer peripheral edge of the light passage hole and a substrate edge of the light transmissive substrate by substrate end points, a distance between the two points on the outer peripheral edge of the light passage hole by "d," and a distance between the substrate end points by "a," a relationship of $a/d \geq 1.6$ is fulfilled.

In the case in which the pressure of the internal space is reduced, in particular in the vacuum state or the state near to the vacuum state, the light transmissive substrate is subjected to the stress urging the light transmissive substrate to be deflected toward the internal space. In the light transmissive substrate disposed with respect to the light passage hole on the light entrance side, if deflection occurs due to the stress described above, the incident light is refracted by the light transmissive substrate to thereby be radially spread, and then enters the interference filter. In this case, the light path length of the light, on which the multiple interferences is caused in the inter-reflecting film gap, is varied in accordance with the angle of the light entering the interference filter. Therefore, it results that many light components with wavelengths different from the target wavelength are included in the light emitted by the interference filter, and there arises a problem that the half bandwidth is broadened and the resolution is degraded.

In contrast, in the configuration described above, the sizes of the light passage hole and the light transmissive substrate are set so that the distance "d" between the two points on the outer peripheral edge of the light passage hole and the distance "a" between the substrate end points in the light transmissive substrate fulfill the relationship of $a/d \geq 1.6$.

Here, if $a/d < 1.6$ is exists, the deflection amount of the light transmissive substrate increases, and the resolution by the interference filter is significantly degraded. In contrast, if the relationship of $a/d \geq 1.6$ is fulfilled as in this aspect of the invention, the deflection amount of the light transmissive substrate can be reduced to the minimum value, and thus the degradation in resolution of the interference filter can be suppressed. In particular in the case in which the relationship of $a/d \geq 2.0$ is fulfilled, the deflection of the light transmissive substrate almost vanishes, and thus the degradation in resolution of the interference filter can more surely be prevented.

In the optical filter device according to the above aspect of the invention, it is preferable that the interference filter has an electrode section, and the base substrate has an interior surface terminal section disposed on a lid-opposed surface opposed to the lid, and electrically connected to the electrode section, and an exterior surface terminal section disposed on a base exterior surface opposite to the lid-opposed surface, and electrically connected to the interior surface terminal section.

It should be noted that as the electrode section, there can be cited, for example, an electrode for supplying electricity to an electrically driven actuator for changing the inter-reflecting film gap, and an electrode for detecting the electrical charge of the capacitance electrode for measuring the dimension of the inter-reflecting film gap.

According to this configuration, the interior surface terminal section disposed on the lid-opposed surface of the base substrate and the exterior surface terminal section disposed on the base exterior surface are electrically connected to each other, and the electrode section of the interference filter and the interior surface terminal section are electrically connected to each other. Therefore, by performing the wiring on the exterior surface terminal section formed on the base exterior surface side of the base substrate, the electrical signal can be transmitted and received to and from the interference filter housed in the internal space.

Further, since the external terminal sections can be collected on the base exterior surface as one surface side of the base substrate, the wiring work to the optical filter device can be simplified.

In the optical filter device according to the above aspect of the invention, it is preferable that the base substrate has a through hole disposed from the lid-opposed surface to the base exterior surface, and a conductive member with which the through hole is filled, and the interior surface terminal section and the exterior surface terminal section are electrically connected via the conductive member.

In this configuration, since the through hole is filled with the conductive member, it is possible to connect the interior surface terminal section and the exterior surface terminal section each other while keeping the airtightness of the internal space. On this occasion, by making the conductive member have direct contact with the interior surface terminal section and the exterior surface terminal section to thereby be connected to each other, the wiring reliability can be enhanced.

In the optical filter device according to the above aspect of the invention, it is preferable that at least one hole penetrating through at least one of the base substrate and the lid and a seal member adapted to seal the hole are provided to at least one of the base substrate and the lid.

In this configuration, since the hole is provided to the base substrate and the lid, by releasing the air in the internal space through the hole after performing the bonding between the light transmissive substrate and the lid, it is possible to set the pressure of the internal space to the state lower than the atmospheric pressure. Therefore, it is not required to perform the bonding between the light transmissive substrate and the lid in the reduced pressure environment or the vacuum environment, and if the bonding work such as soldering is performed manually, the workability can be enhanced.

In the optical filter device according to the above aspect of the invention, it is preferable that the interference filter has a non-light transmissive member having a ring-like shape disposed on a light entrance surface which the light having passed through the light passage hole enters.

In this configuration, since the non-light transmissive member is formed to have a ring-like shape, it is possible to make the inner peripheral edge function as an aperture. Thus, it is possible to define the angle of the light to be input to the optical filter device from the light passage hole, and thus the stray light can be prevented to thereby obtain the highly accurate spectral characteristics. Further, by providing the non-light transmissive member to the interference filter, it is also possible to enhance the accuracy of the alignment adjustment of the effective range with respect to the first reflecting film and the second reflecting film.

An optical module according to one aspect of the invention includes an interference filter having a first substrate, a second substrate opposed to the first substrate, a first reflecting film provided to the first substrate, and a second reflecting film provided to the second substrate and opposed to the first reflecting film across an inter-reflecting film gap, a housing adapted to house the interference filter, and a detection section adapted to detect the light emitted by the interference filter, the housing is provided with a base substrate, and a lid bonded to the base substrate, and forming an internal space capable of housing the interference filter between the lid and the base substrate, at least one of the base substrate and the lid is provided with a light passage hole in an area opposed to the first reflecting film and the second reflecting film, the housing has a light transmissive substrate adapted to cover the light passage hole, a substrate edge of the light transmissive substrate is located outside an outer peripheral edge of the light passage hole in a plan view of the light transmissive substrate viewed from a thickness direction of the light transmissive substrate, and the light transmissive substrate is bonded to at least the one of the base substrate and the lid provided with the light passage hole in an area extending from the outer peripheral edge of the light passage hole to the substrate edge in the plan view.

According to this aspect of the invention, similarly to the above aspect of the invention, the airtightness of the internal space of the inside of the housing is preferable, and the invasion of water particles and electrically-charged particles can be prevented. Therefore, the deterioration of the reflecting film and so on due to the invasion of such particles can be prevented, the light with the target wavelength can be emitted by the interference filter at high resolution, and accurate light intensity detection can be performed by integrally controlling the interference filter and the detection section.

An electronic apparatus according to one aspect of the invention includes an interference filter having a first substrate, a second substrate opposed to the first substrate, a first reflecting film provided to the first substrate, and a second reflecting film provided to the second substrate and opposed to the first reflecting film across an inter-reflecting film gap, and a housing adapted to house the interference filter, the housing is provided with a base substrate, and a lid bonded to the base substrate, and forming an internal space capable of housing the interference filter between the lid and the base substrate, at least one of the base substrate and the lid is provided with a light passage hole in an area opposed to the first reflecting film and the second reflecting film, the housing has a light transmissive substrate adapted to cover the light passage hole, a substrate edge of the light transmissive substrate is located outside an outer peripheral edge of the light passage hole in a plan view of the light transmissive substrate viewed from a thickness direction of the light transmissive substrate, and the light transmissive substrate is bonded to at least the one of the base substrate and the lid provided with the light passage hole in an area extending from the outer peripheral edge of the light passage hole to the substrate edge in the plan view.

According to this aspect of the invention, similarly to the above aspect of the invention, the airtightness of the internal space of the inside of the housing is preferable, and the invasion of water particles and electrically-charged particles can be prevented. Therefore, the deterioration of the reflecting film and so on due to the invasion of such particles can be prevented, the light with the target wavelength can be emitted by the interference filter at high resolution, and a highly accurate electronic processing (e.g., colorimetric measurement and componential analysis) can be performed using the light thus emitted.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

A first embodiment of the invention will hereinafter be explained with reference to the accompanying drawings.

1. Configuration of Optical Filter Device

Figure 1:
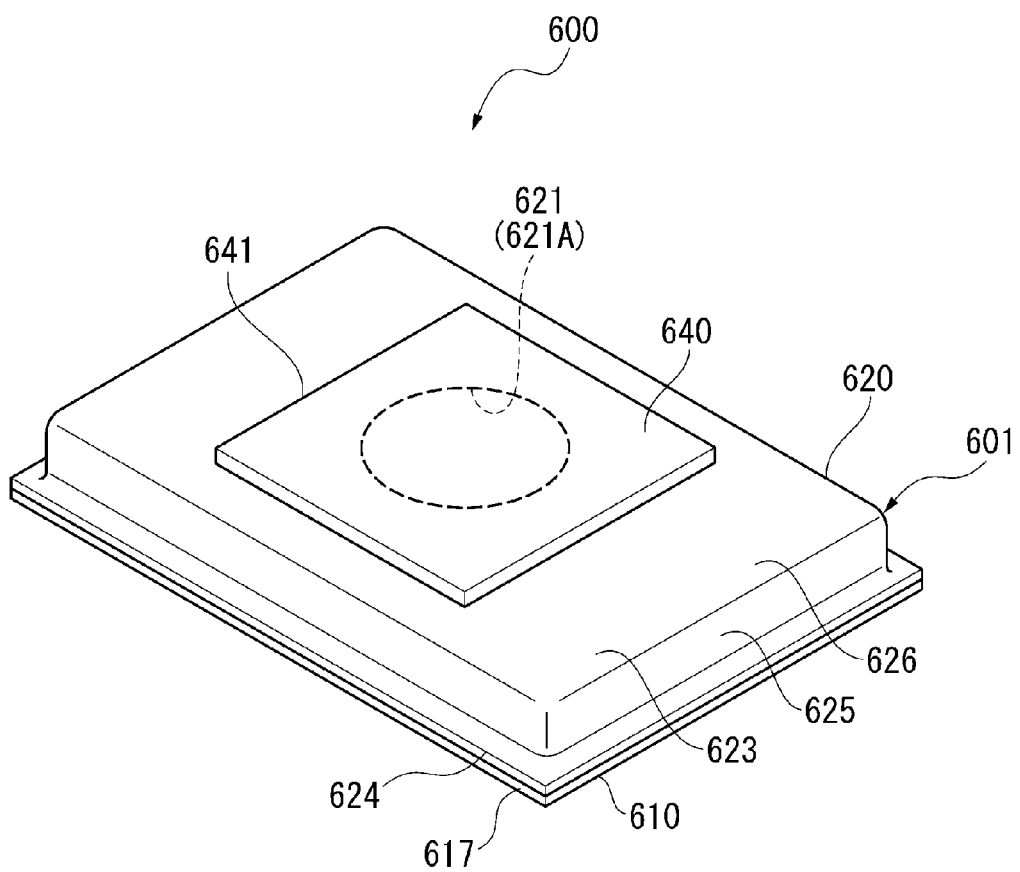
FIG. 1 is a perspective view showing a schematic configuration of an optical filter device according to a first embodiment of the invention.
Figure 2:
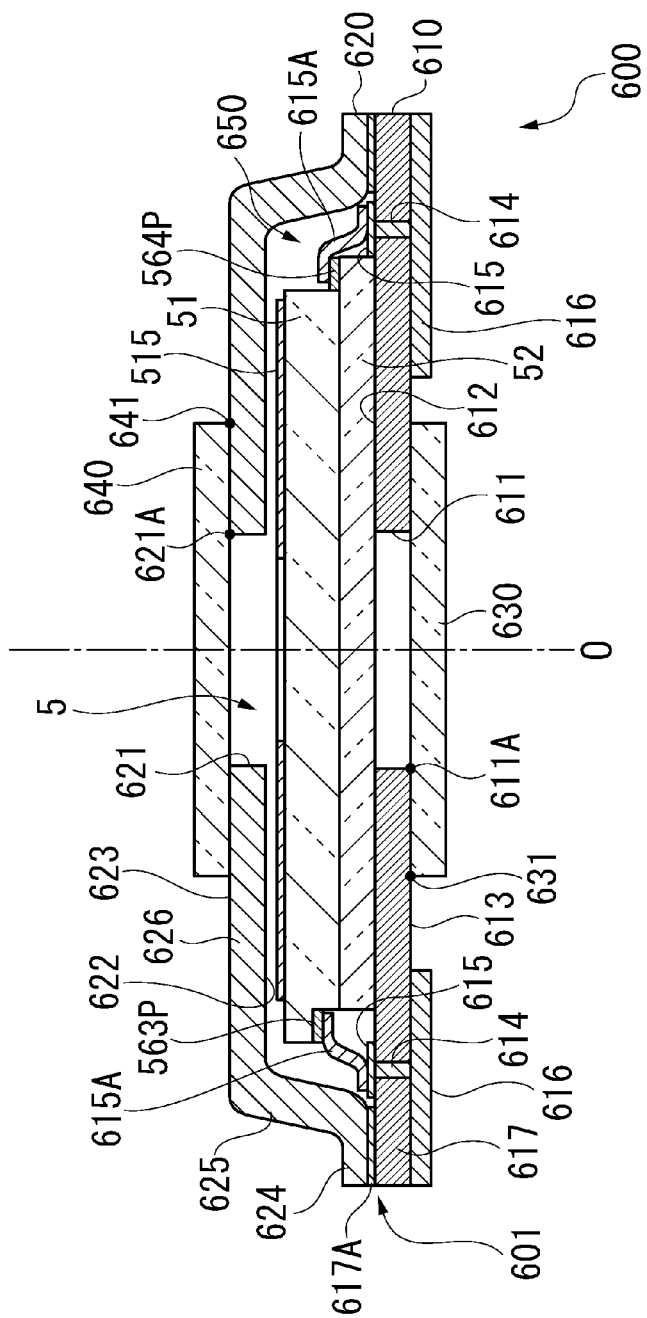
FIG. 2 is a cross-sectional view showing a schematic configuration of the optical filter device according to the first embodiment.

FIG. 1 is a perspective view showing a schematic configuration of an optical filter device 600 according to the present embodiment of the invention. FIG. 2 is a cross-sectional view of the optical filter device 600.

The optical filter device 600 is a device for taking out light with a predetermined target wavelength from incident test target light and then emitting the light thus emitted, and is provided with a housing 601, and a variable wavelength interference filter 5 (see FIG. 2) housed in the housing 601. Such an optical filter device 600 can be incorporated in an optical module such as a colorimetric sensor, or an electronic apparatus such as a colorimetric device or a gas analyzing device. It should be noted that the configurations of the optical module and the electronic apparatus equipped with the optical filter device 600 will be explained in a second embodiment described later.

2. Configuration of Variable Wavelength Interference Filter

Figure 3:
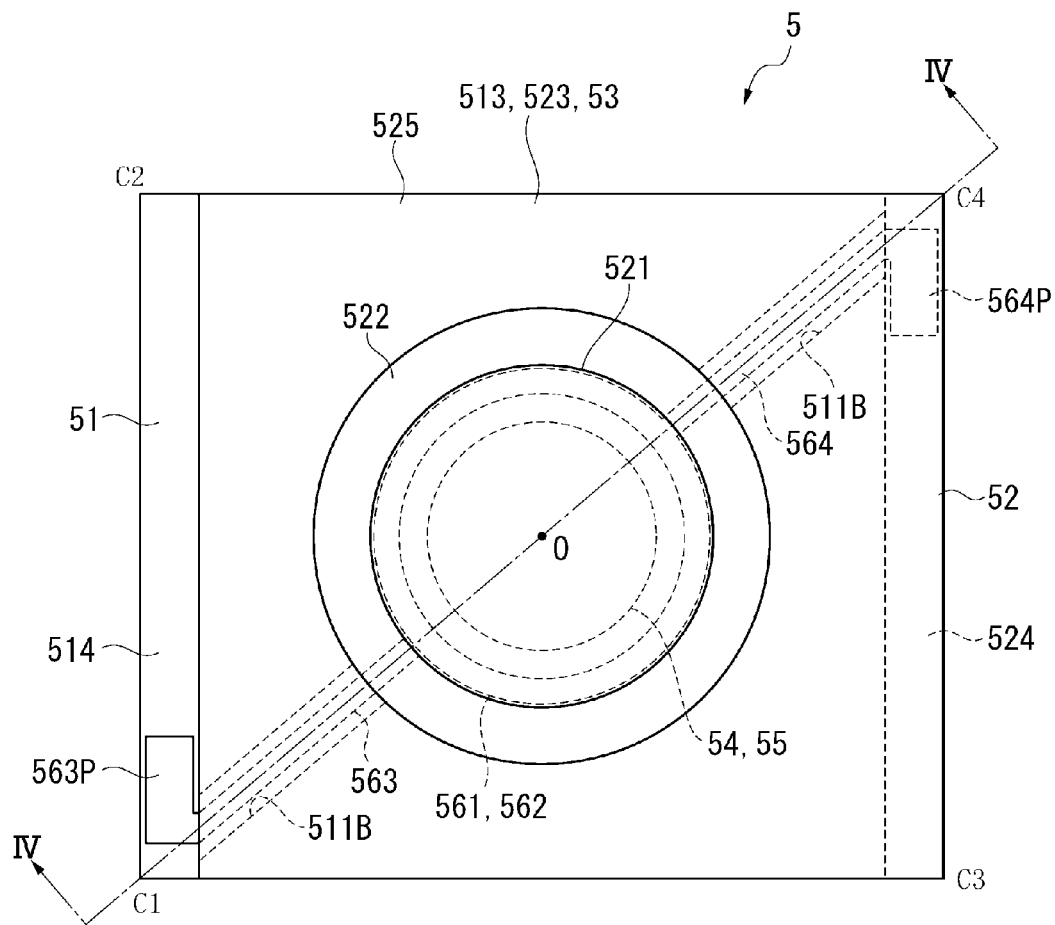
FIG. 3 is a plan view showing a schematic configuration of an interference filter housed in the optical filter device according to the first embodiment.
Figure 4:
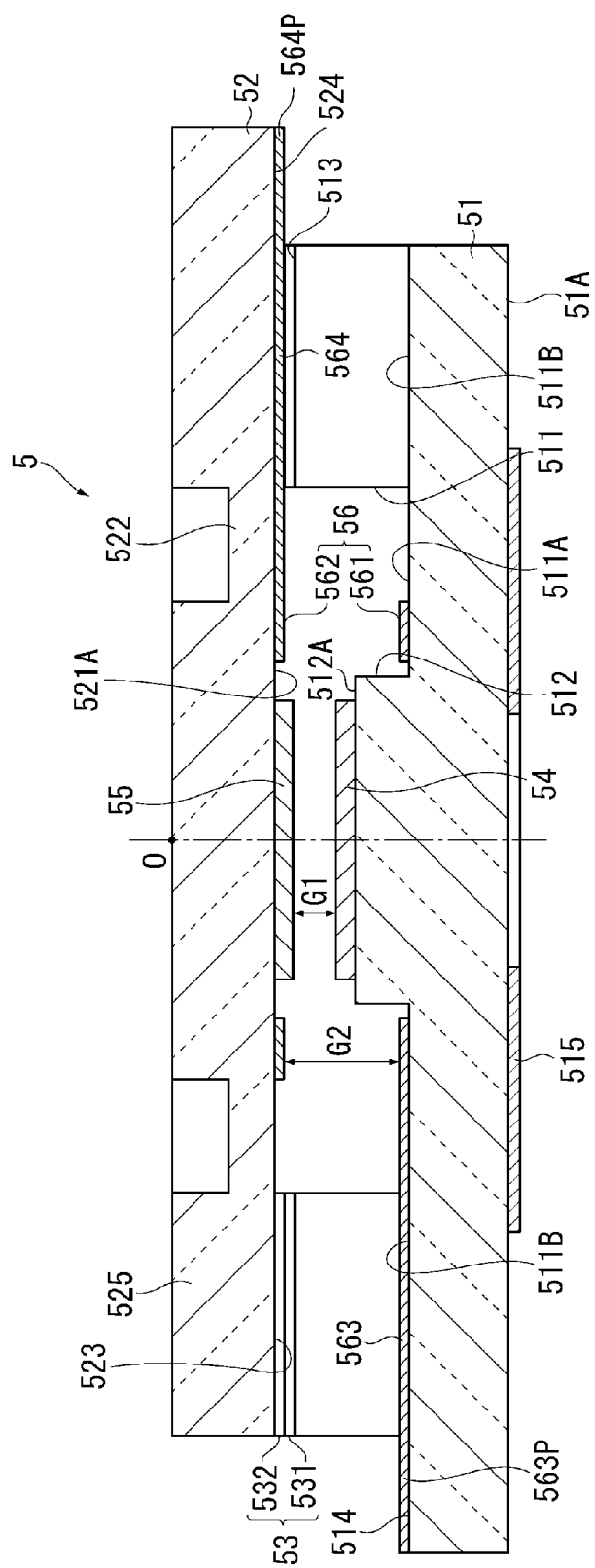
FIG. 4 is a cross-sectional view showing a schematic configuration of the interference filter according to the first embodiment.

The variable wavelength interference filter 5 constitutes the interference filter according to the embodiment of the invention. FIG. 3 is a plan view showing a schematic configuration of the variable wavelength interference filter 5 provided to the optical filter device 600, and FIG. 4 is a cross-sectional view showing the schematic configuration of the variable wavelength interference filter 5 when drawing a cross-sectional view along the line IV-IV shown in FIG. 3.

As shown in FIG. 3, the variable wavelength interference filter 5 is an optical member having, for example, a rectangular shape. The variable wavelength interference filter 5 is provided with a stationary substrate 51 as a first substrate, and a movable substrate 52 as a second substrate. The stationary substrate 51 and the movable substrate 52 are each made of any of a variety of types of glass such as soda glass, crystalline glass, quartz glass, lead glass, potassium glass, borosilicate glass, or alkali-free glass, or a quartz crystal. Further, the stationary substrate 51 and the movable substrate 52 are configured integrally by bonding a first bonding section 513 of the stationary substrate 513 and a second bonding section 523 of the movable substrate 52 to each other with bonding films 53 (a first bonding film 531 and a second bonding film 532) each formed of, for example, a plasma polymerization film consisting primary of, for example, siloxane.

It should be noted that in the explanation below, the plan view from the thickness direction of the stationary substrate 51 or the movable substrate 52, namely the plan view of the variable wavelength interference filter 5 viewed from the stacking direction of the stationary substrate 51, the bonding film 53, and the movable substrate 52, is referred to as the filter plan view.

The stationary substrate 51 is provided with a stationary reflecting film 54 constituting a first reflecting film, and the movable substrate 52 is provided with a movable reflecting film 55 constituting a second reflecting film. The stationary reflecting film 54 and the movable reflecting film 55 are disposed so as to be opposed to each other (face each other) across an inter-reflecting film gap G1. Further, the variable wavelength interference filter 5 is provided with an electrostatic actuator 56 used for adjusting the dimension of the inter-reflecting film gap G1 (the distance between the reflecting films). The electrostatic actuator 56 is constituted by a stationary electrode 561 provided to the stationary substrate 51 and a movable electrode 562 provided to the movable substrate 52. The stationary electrode 561 and the movable electrode 562 are opposed to each other across an inter-electrode gap G2 (G2>G1). Here, there can be adopted a configuration of disposing these electrodes 561, 562 directly on the surfaces of the stationary substrate 51 and the movable substrate 52, respectively, or a configuration of disposing them via other film members.

It should be noted that although in the present embodiment, a configuration in which the inter-reflecting film gap G1 is formed to be smaller than the inter-electrode gap G2 is described as an example, it is also possible to form the inter-reflecting film gap G1 to be larger than the inter-electrode gap G2 depending on the wavelength band in which the variable wavelength interference filter 5 transmits the light.

In the filter plan view, one side (e.g., the side between the vertex C1 and the vertex C2 in FIG. 3) of the stationary substrate 51 projects to the outside of the movable substrate 52. Out of the projected portion, the surface exposed when viewing the variable wavelength interference filter 5 from the movable substrate 52 side constitutes a first electrical installation surface 514.

Further, in the filter plan view, one side (the side between the vertex C3 and the vertex C4) opposed to the first electrical installation surface 514 out of the sides of the movable substrate 52 projects to the outside of the stationary substrate 51. Out of the projected portion, the surface exposed when viewing the variable wavelength interference filter 5 from the stationary substrate 51 side constitutes a second electrical installation surface 524.

2-1. Configuration of Stationary Substrate

The stationary substrate 51 is formed by processing a glass substrate formed to have a thickness of, for example, 500 μm. Specifically, as shown in FIG. 4, the stationary substrate 51 is provided with an electrode arrangement groove 511 and a reflecting film installation section 512 by etching. The stationary substrate 51 is formed to have a thickness dimension larger than that of the movable substrate 52, and there is no deflection of the stationary substrate 51 due to the electrostatic attractive force when applying a voltage between the stationary electrode 561 and the movable electrode 562, or the internal stress of the stationary electrode 561.

The electrode arrangement groove 511 is formed to have a ring-like shape cantered on the center point O of the variable wavelength interference filter 5 in the filter plan view. The reflecting film installation section 512 is formed so as to protrude toward the movable substrate 52 from the central portion of the electrode arrangement groove 511 in the plan view described above. Here, the bottom surface of the electrode arrangement groove 511 forms an electrode installation surface 511A on which the stationary electrode 561 is disposed. Further, the projection tip surface of the reflecting film installation section 512 forms a reflecting film installation surface 512A.

Further, the stationary substrate 51 is provided with electrode extraction grooves 511B respectively extending from the electrode arrangement groove 511 toward the first electrical installation surface 514 and the second electrical installation surface 524.

The electrode installation surface 511A of the electrode arrangement groove 511 is provided with the stationary electrode 561. The stationary electrode 561 is disposed in an area out of the electrode installation surface 511A, the area being opposed to the movable electrode 562 of a movable section 521 described later. Further, it is also possible to adopt the configuration in which an insulating film for providing an insulation property between the stationary electrode 561 and the movable electrode 562 is stacked on the stationary electrode 561.

Further, the stationary substrate 51 is provided with a stationary extraction electrode 563 extending from the outer peripheral edge of the stationary electrode 561 to the first electrical installation surface 514 through the electrode extraction groove 511B. The extending tip portion (the part located at the vertex C2 of the stationary substrate 51) of the stationary extraction electrode 563 forms a stationary electrode pad 563P on the first electrical installation surface 514.

It should be noted that although in the present embodiment there is shown a configuration of providing the single stationary electrode 561 to the electrode installation surface 511A, it is also possible to adopt, for example, a configuration (a dual electrode structure) having two concentric electrodes centered on the planar center point O.

As described above, the reflecting film installation section 512 is formed to have a roughly columnar shape coaxial with the electrode arrangement groove 511 and having a diameter smaller than that of the electrode arrangement groove 511, and is provided with the reflecting film installation surface 512A opposed to the movable substrate 52.

As shown in FIG. 4, the stationary reflecting film 54 is installed in the reflecting film installation section 512. As the stationary reflecting film 54, a metal film made of, for example, Ag, or an alloy film made of, for example, an Ag alloy can be used. Further, it is also possible to use a dielectric multilayer film with a high refractive index layer made of, for example, $TiO_2$, and a low refractive index layer made of, for example, $SiO_2$. Further, it is also possible to use a reflecting film obtained by stacking a metal film (or an alloy film) on a dielectric multilayer film, a reflecting film obtained by stacking a dielectric multilayer film on a metal film (or an alloy film), a reflecting film obtained by laminating a single refractive layer (made of, e.g., $TiO_2$ or $SiO_2$) and a metal film (or an alloy film) with each other, and so on.

Further, it is also possible to form an antireflection film on the light entrance surface 51A (the surface not provided with the stationary reflecting film 54) of the stationary substrate 51 at a position corresponding to the stationary reflecting film 54. The antireflection film can be formed by alternately stacking low refractive index films and high refractive index films, decreases the reflectance of the visible light on the surface of the stationary substrate 51, and increases the transmittance thereof.

Further, the light entrance surface 51A of the stationary substrate 51 is provided with a non-light transmissive member 515 made of, for example, Cr. The non-light transmissive member 515 is formed to have a ring-like shape, and more preferably, an annular shape. Further, the inner diameter of the ring of the non-light transmissive member 515 is set to an effective diameter for causing optical interference with the stationary reflecting film 54 and the movable reflecting film 55. Thus, the non-light transmissive member 515 functions as an aperture for narrowing the incident light having entered the optical filter device 600.

Further, the surface not provided with the electrode arrangement groove 511, the reflecting film installation section 512, and the electrode extraction grooves 511B by etching out of the surfaces of the stationary substrate 51 opposed to the movable substrate 52 constitutes a first bonding section 513. The first bonding section 513 is provided with a first bonding film 531, and by bonding the first bonding film 531 to a second bonding film 532 provided to the movable substrate 52, the stationary substrate 51 and the movable substrate 52 are bonded to each other as described above.

2-2. Configuration of Movable Substrate

The movable substrate 52 is formed by processing a glass substrate formed to have a thickness of, for example, 200 μm.

Specifically, the movable substrate 52 is provided with the movable section 521 having a circular shape centered on the planar center point O in the filter plan view shown in FIG. 3, a holding section 522 disposed outside the movable section 521 and for holding the movable section 521, and a substrate peripheral section 525 disposed outside the holding section 522.

The movable section 521 is formed to have a thickness dimension larger than that of the holding section 522, and is formed in the present embodiment, for example, to have the same thickness dimension as that of the movable substrate 52. The movable section 521 is formed to have a diameter larger than at least the diameter of the outer peripheral edge of the reflecting film installation surface 512A in the filter plan view. Further, the movable section 521 is provided with the movable electrode 562 and the movable reflecting film 55.

It should be noted that it is also possible to form an antireflection film on the opposite surface of the movable section 521 similarly to the stationary substrate 51 to the case of the stationary substrate 51. Such an antireflection film can be formed by alternately stacking low refractive index films and high refractive index films, and is capable of decreasing the reflectance of the visible light on the surface of the stationary substrate 52, and increasing the transmittance thereof.

The movable electrode 562 is opposed to the stationary electrode 561 across the inter-electrode gap G2, and is formed to have a ring-like shape, which is the same shape as that of the stationary electrode 561. Further, the movable substrate 52 is provided with a movable extraction electrode 564 extending from the outer peripheral edge of the movable electrode 562 toward the second electrical installation surface 524. The extending tip portion (the part located at the vertex C1 of the movable substrate 52) of the movable extraction electrode 564 forms a movable electrode pad 564P in the second electrical installation surface 524.

The movable reflecting film 55 is disposed at the central portion of a movable surface 521A of the movable section 521 so as to be opposed to the stationary reflecting film 54 across the inter-reflecting film gap G1. As the movable reflecting film 55, a reflecting film having the same configuration as that of the stationary reflecting film 54 described above is used.

The holding section 522 is a diaphragm surrounding the periphery of the movable section 521, and is formed to have a thickness dimension smaller than that of the movable section 521.

Such a holding section 522 is more easily deflected than the movable section 521, and it becomes possible to displace the movable section 521 toward the stationary substrate 51 with a weak electrostatic attractive force. Since the movable section 521 has a larger thickness dimension and higher rigidity than those of the holding section 522, the shape variation of the movable section 521 does not occur even in the case in which the holding section 522 is pulled toward the stationary substrate 51 due to the electrostatic attractive force. Therefore, deflection of the movable reflecting film 55 provided to the movable section 521 does not occur, and it becomes possible to always keep the stationary reflecting film 54 and the movable reflecting film 55 in a parallel state.

It should be noted that although in the present embodiment the holding section 522 having a diaphragm shape is shown as an example, the shape is not limited thereto, but a configuration of, for example, providing beam-like holding sections arranged at regular angular intervals centered on the planar center point O can also be adopted.

As described above, the substrate peripheral section 525 is disposed on the outer side of the holding section 522 in the filter plan view. The surface of the substrate peripheral section 525 opposed to the stationary substrate 51 is provided with the second bonding section 523 opposed to the first bonding section 513. Further, the second bonding section 523 is provided with the second bonding film 532, and as described above, by bonding the second bonding film 532 to the first bonding film 531, the stationary substrate 51 and the movable substrate 52 are bonded to each other.

3. Configuration of Housing

Going back to FIGS. 1 and 2, the housing 601 is provided with a base substrate 610, a lid 620, a base-side glass substrate 630 (a light transmissive substrate), and a lid-side glass substrate 640 (a light transmissive substrate).

The base substrate 610 is formed of, for example, a single layer ceramic substrate. The base substrate 610 is provided with the movable substrate 52 of the variable wavelength interference filter 5. As a method of installation of the movable substrate 52 to the base substrate 610, it is possible to adopt a method of disposing it via, for example, an adhesive layer, or a method of disposing it by fitting it to, for example, another fixation member.

The base section 610 is provided with a light entrance hole 611 formed in an area opposed to the reflecting films (the stationary reflecting film 54, the movable reflecting film 55) of the variable wavelength interference filter 5.

Abase interior surface 612 (a lid-opposed surface) of the base substrate 610 opposed to the lid 620 is provided with internal terminal sections 615 to be connected to the respective electrode pads 563P, 564P on the first electrical installation surface 514 and the second electrical installation surface 524 of the variable wavelength interference filter 5. It should be noted that the connection between each of the electrode pads 563P, 564P and the internal terminal section 615 can be achieved using, for example, a flexible printed circuit (FPC) 615A, and bonding therebetween is achieved using, for example, Ag paste, an anisotropic conductive film (ACF), and anisotropic conductive paste (ACP). It should be noted that Ag paste with little gas emission is preferably used for keeping the internal space 650 in the vacuum state. It should be noted that wiring connection with, for example, wire bonding can also be performed besides the connection using the FPCs 615A.

Further, the base substrate 610 is provided with through holes 614 formed at positions where the respective internal terminal sections 615 are disposed, and the internal terminal sections 615 are connected to external terminal sections 616 disposed on a base exterior surface 613 of the base substrate 610 on the opposite side to the base interior surface 612 via the through holes 614, respectively. Here, the through holes 614 are filled with a metal material (e.g., the Ag paste) for connecting the internal terminal sections 615 and the external terminal sections 616 to thereby keep the airtightness of the internal space 650 of the housing 601.

Further, the outer peripheral portion of the base substrate 610 is provided with a base bonding section 617 to be bonded to the lid 620.

As shown in FIGS. 1 and 2, the lid 620 is provided with a lid bonding section 624 to be bonded to the base bonding section 617 of the base substrate 610, a sidewall section 625 continuous from the lid bonding section 624 and rising in the direction extending away from the base substrate 610, and a top surface section 626 continuous from the sidewall section 625 and covering the stationary substrate 51 side of the variable wavelength interference filter 5. The lid 620 can be formed of an alloy such as kovar, or metal.

The lid 620 is adhesively bonded to the base substrate 610 by the lid bonding section 624 and the base bonding section 617 of the base substrate 610 bonded to each other.

As the bonding method, there can be cited, for example, soldering with brazing silver or the like, sealing with a eutectic alloy layer, welding with low-melting-point glass, glass adhesion, glass frit bonding, and adhesion with epoxy resin, besides laser welding. These bonding methods can arbitrarily be selected in accordance with the materials of the base substrate 610 and the lid 620, bonding environment, and so on.

In the present embodiment, a bonding pattern 617A formed of, for example, Ni and Au is formed on the base bonding section 617 of the base substrate 610, then the bonding pattern 617A and the lid bonding section 624 are irradiated with a high-power laser (e.g., a YAG laser) to thereby perform the laser bonding.

The top surface section 626 of the lid 620 is set to be parallel to the base substrate 610. The top surface section 626 is provided with a light passage hole 621 formed in an area opposed to the reflecting films 54, 55 of the variable wavelength interference filter 5.

Here, in the present embodiment, light enters from the light passage hole 621 of the lid 620, and the light emitted by the variable wavelength interference filter 5 is emitted from the light passage hole 611 of the base substrate 610. In such a configuration as described above, only the light corresponding to the effective diameter of the non-light transmissive member 515 provided to the light entrance surface 51A of the variable wavelength interference filter 5 out of the light having entered from the light passage hole 621 enters the stationary reflecting film 54 and the movable reflecting film 55. In particular, the shapes of the substrates 51, 52 of the variable wavelength interference filter 5 are formed by etching, and a curved part is formed in the etched part due to the influence of the side etching. If the light enters such a curved part, the light might be emitted from the light passage hole 611 as stray light in some cases. In contrast, in the present embodiment, such stray light can be prevented from occurring by the non-light transmissive member 515, and it becomes possible to selectively emit the light with the desired wavelength.

The base-side glass substrate 630 is a glass substrate bonded to the base exterior surface 613 side of the base substrate 610 so as to cover the light passage hole 611. The base-side glass substrate 630 is formed to have a size larger than that of the light passage hole 611, and is arranged so that the planar central point O of the base-side glass substrate 630 coincides with the planar center point O of the light passage hole 611. It should be noted that the planar center point O coincides with the planar center point O of the variable wavelength interference filter 5, and further coincides with the planar center point O of the inner peripheral edges of the ring of the stationary reflecting film 54, the movable reflecting film 55, and the non-light transmissive member 515. Further, the base-side glass substrate 630 is bonded to the base substrate 610 in an area (an area extending from the outer peripheral edge 611A to the substrate edge 631 of the base-side glass substrate 630) outside the outer peripheral edge 611A of the light passage hole 611 in the plan view of the optical filter device 600 viewed from the thickness direction of the base substrate 610 (the base-side glass substrate 630).

Similarly, the lid-side glass substrate 640 is a glass substrate bonded to the lid 620 on the lid exterior surface 623 side opposite to the light passage hole 621 opposed to the base substrate 610 so as to cover the light passage hole 621. The lid-side glass substrate 640 is formed to have a size larger than that of the light passage hole 621, and is arranged so that the planar central point O of the lid-side glass substrate 640 coincides with the planar center point O of the light passage hole 621. Further, the lid-side glass substrate 640 is bonded to the lid 620 in an area (an area extending from the outer peripheral edge 621A to the substrate edge 641 of the lid-side glass substrate 640) outside the outer peripheral edge 621A of the light passage hole 621 in the plan view of the optical filter device 600 viewed from the thickness direction of the base substrate 610 (the lid-side glass substrate 640).

As the method of bonding the base substrate 610 and the base-side glass substrate 630 to each other, and the method of bonding the lid 620 and the lid-side glass substrate 640 to each other, there can be used the glass frit bonding using a glass frit, which is a scrap of glass obtained by melting the glass material at high temperature and then rapidly cooling it. In such glass frit bonding, no gap occurs in the bonded area, and it is possible to keep the internal space 650 in the vacuum state by using the glass frit with little gas emission. It should be noted that the bonding method is not limited to the glass frit bonding, but the bonding method such as the welding using the low-melting-point glass or glass sealing can also be adopted. Further, although not suitable for keeping the vacuum state of the internal space 650, the adhesion with epoxy resin or the like can also be performed if the purpose is only for preventing foreign matters from entering the internal space 650, for example.

As described above, in the optical filter device 600 of the present embodiment, the housing 601 has the internal space 650 of the housing 601 kept airtight due to the bonding between the base substrate 610 and the lid 620, the bonding between the base substrate 610 and the base-side glass substrate 630, and the bonding between the lid 620 and the lid-side glass substrate 640. Further, in the present embodiment, the internal space 650 is kept in the vacuum state.

By keeping the internal space 650 in the vacuum state as described above, no air resistance occurs when moving the movable section 521 of the variable wavelength interference filter 5, and it is possible to make the response preferable.

Size Setting of Base-Side Glass Substrate 630 and Lid-Side Glass Substrate 640

As described above, if the internal space 650 is set to the vacuum state, a stress occurs urging the base-side glass substrate 630 and the lid-side glass substrate 640 to be deflected toward the internal space 650.

Figure 5:
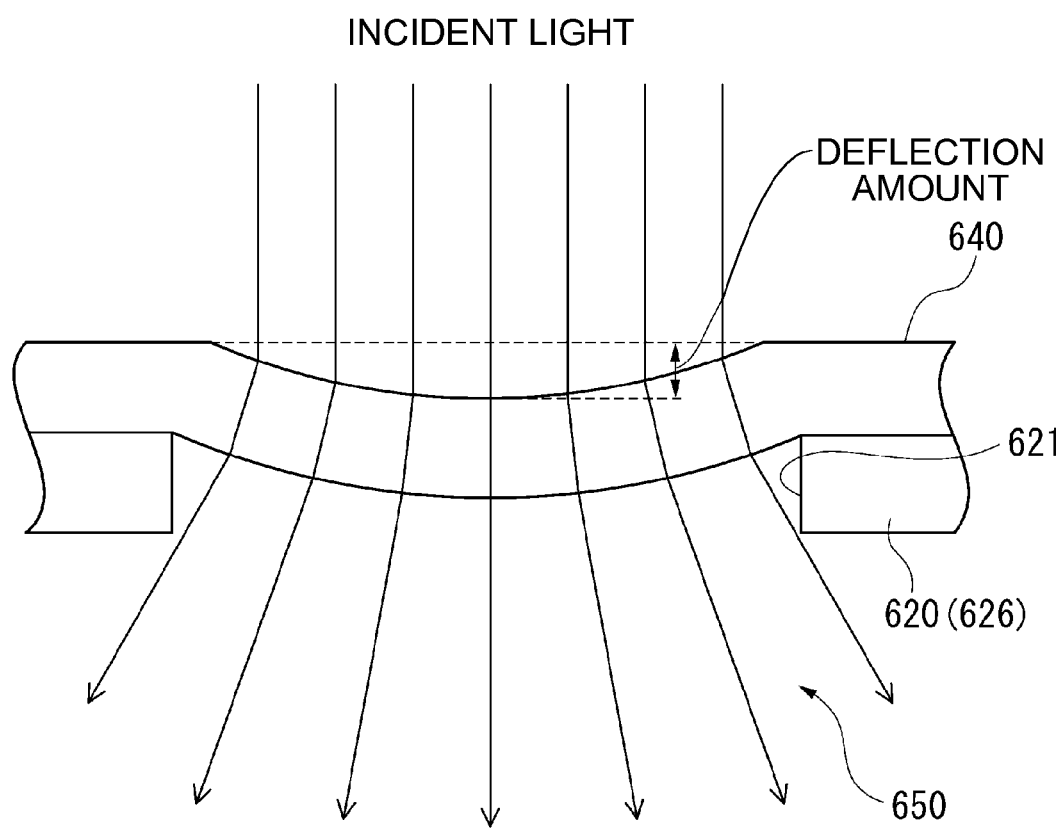
FIG. 5 is a diagram showing a path of incident light in the case in which a lid-side glass substrate is deflected due to a vacuum stress.

FIG. 5 is a diagram showing a path of the incident light in the case in which the lid-side glass substrate 640 is deflected due to the vacuum stress.

As shown in FIG. 5, when the lid-side glass substrate 640 located in particular on the light entrance side is deflected to have a curved surface due to the stress, the incident light is refracted when passing through the lid-side glass substrate 640, and the entrance angle of the light to the variable wavelength interference filter 5 is varied. On this occasion, it results that many light components with wavelengths different from the target wavelength are included in the light emitted by the variable wavelength interference filter 5, and there arises a problem of degradation in resolution.

In contrast, according to the present embodiment, the sizes of the base-side glass substrate 630 and the lid-side glass substrate 640 are determined as described below.

Figure 6A:
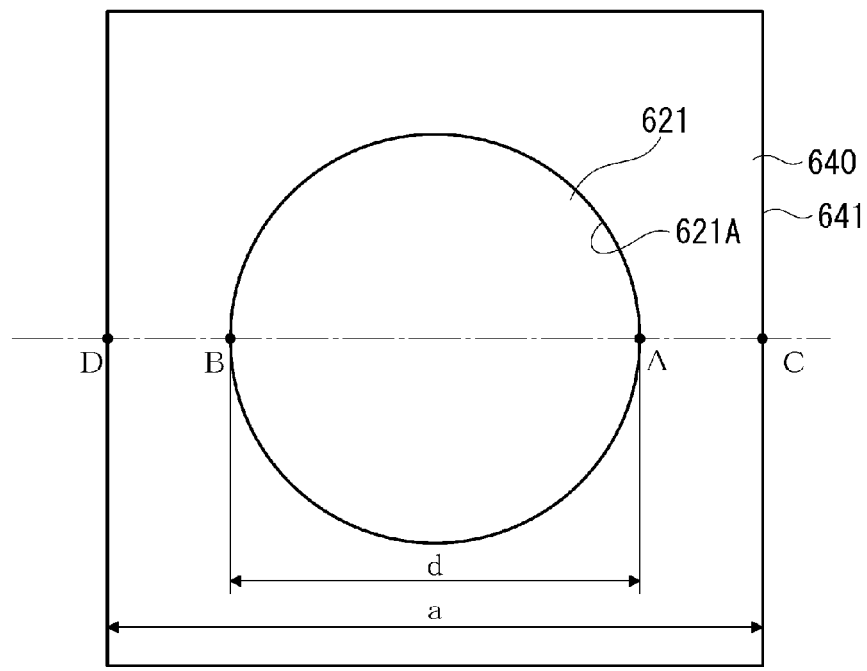
FIG. 6A is a diagram for explaining size setting of the lid-side glass substrate.

FIG. 6A is a diagram for explaining the size setting of the lid-side glass substrate 640. It should be noted that although the lid-side glass substrate 640 will be explained here, it is preferable that the base-side glass substrate 630 is also set to have substantially the same size.

In FIG. 6A, two points on the outer peripheral edge of the lid-side glass substrate 640 are denoted by A, B, and the intersections between the straight line connecting the points A, B and the substrate edge 641 of the lid-side glass substrate 640 are denoted by C, D.

Here, the distance between the points A, B is defined as "d," and the distance between the points C, D is defined as "a," and when experimenting to determine the influence on the optical characteristics of the variable wavelength interference filter 5 while varying the distance "a," the result shown in Table 1 below can be obtained.

TABLE 1

| a/d | Maximum deflection value (μm) | Influence on optical characteristics |
|-----|-------------------------------|--------------------------------------|
| 1.2 | 13.7 | Problematic |
| 1.6 | 11.7 | Allowable |
| 2.0 | 10.7 | No problem |

In the determination of the influence on the optical characteristics of the variable wavelength interference filter 5, whether or not there can be obtained the resolution in a level which does not affect the measurement result in the normal spectroscopic measurement is determined. Specifically, if the half bandwidth of the dispersion spectrum obtained by the variable wavelength interference filter 5 is equal to or higher than 10% with respect to the reference value, it is determined that the influence is "problematic," if the half bandwidth is in a range of 10% through 5% with respect to the reference value, it is determined that the influence is "allowable," and if the half bandwidth is equal to or lower than 5%, it is determined that the influence is "no problem."

In the experiment described above, as shown in Table 1, taking the value of "a/d" of 1.6 as a border value, if the value is lower than 1.6, the maximum deflection value of the lid-side glass substrate 640 is large, and the influence on the optical characteristics is significant, and the resolution is significantly degraded.

In contrast, if the value of "a/d" is equal to or higher than 1.6, the influence on the optical characteristics is small, and in particular in the case in which the value of "a/d" exceeds 2.0, the influence of the deflection of the lid-side glass substrate 640 on the optical characteristics is in a negligible level.

Based on the experimental result described above, in the present embodiment, the sizes of the light passage holes 611, 621, the base-side glass substrate 630, and the lid-side glass substrate 640 are set so to satisfy the condition that the value of "a/d" is equal to 2.0. Therefore, even in the case of setting the internal space 650 to the vacuum state, the deflection of the lid-side glass substrate 640 is negligibly small, and it becomes possible to selectively emit the light with the target wavelength at a high resolution by the variable wavelength interference filter 5.

Figure 6B:
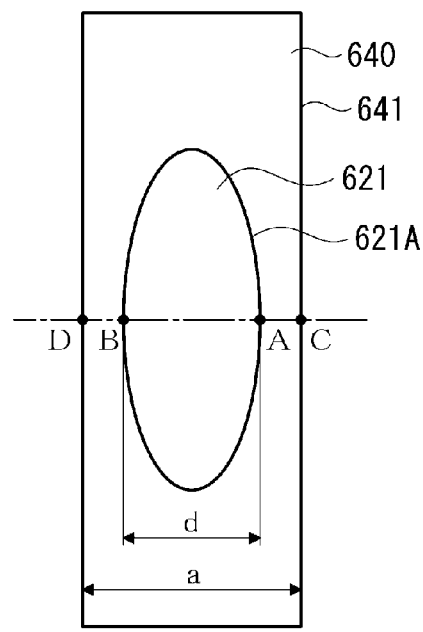
FIG. 6B is a diagram for explaining the size setting of the lid-side glass substrate in the case in which a light passage hole has an elliptical shape.

It should be noted that although the example of the case in which the light passage holes 611, 621 have a circular shape in the plan view is described in the above example, the same can be applied to the case of having a different shape. For example, in the case in which the light passage holes 611, 621 have an elliptical shape as shown in FIG. 6B, it is possible to set the dimension of the lid-side glass substrate 640 (the base-side glass substrate 630) corresponding to the long diameter direction of the elliptical shape and the dimension of the lid-side glass substrate 640 (the base-side glass substrate 630) corresponding to the short diameter direction to the values each fulfilling "a/d≥1.6" in the lid-side glass substrate 640 (the base-side glass substrate 630) (FIG. 6B describes only the dimension in the short diameter direction).

Further, although in the present embodiment the planar center point O of the light passage hole 611 and the planar center point O of the base-side glass substrate 630 are made to coincide with each other, and the planar center point O of the light passage hole 621 and the planar center point O of the lid-side glass substrate 640 are made to coincide with each other, the invention is not limited thereto. For example, it is also possible for the lid-side glass substrate 640 to be eccentrically bonded with respect to the planar center point O of the light passage hole 621. It should be noted that in this case if the distance from the outer peripheral edge 611A of the light passage hole 611 to the substrate edge 641 of the lid-side glass substrate 640 is too short, the lid-side glass substrate 640 might be deflected. In this case, it is sufficient to set the size of the lid-side glass substrate 640 so that the distance (a run-off amount) from the outer peripheral edge 611A to the substrate edge 641 is equal to or longer than "0.3 d."

Method of Manufacturing Optical Filter Device

Next, a method of manufacturing the optical filter device 600 described above will be explained with reference to the accompanying drawings.

Figure 7:
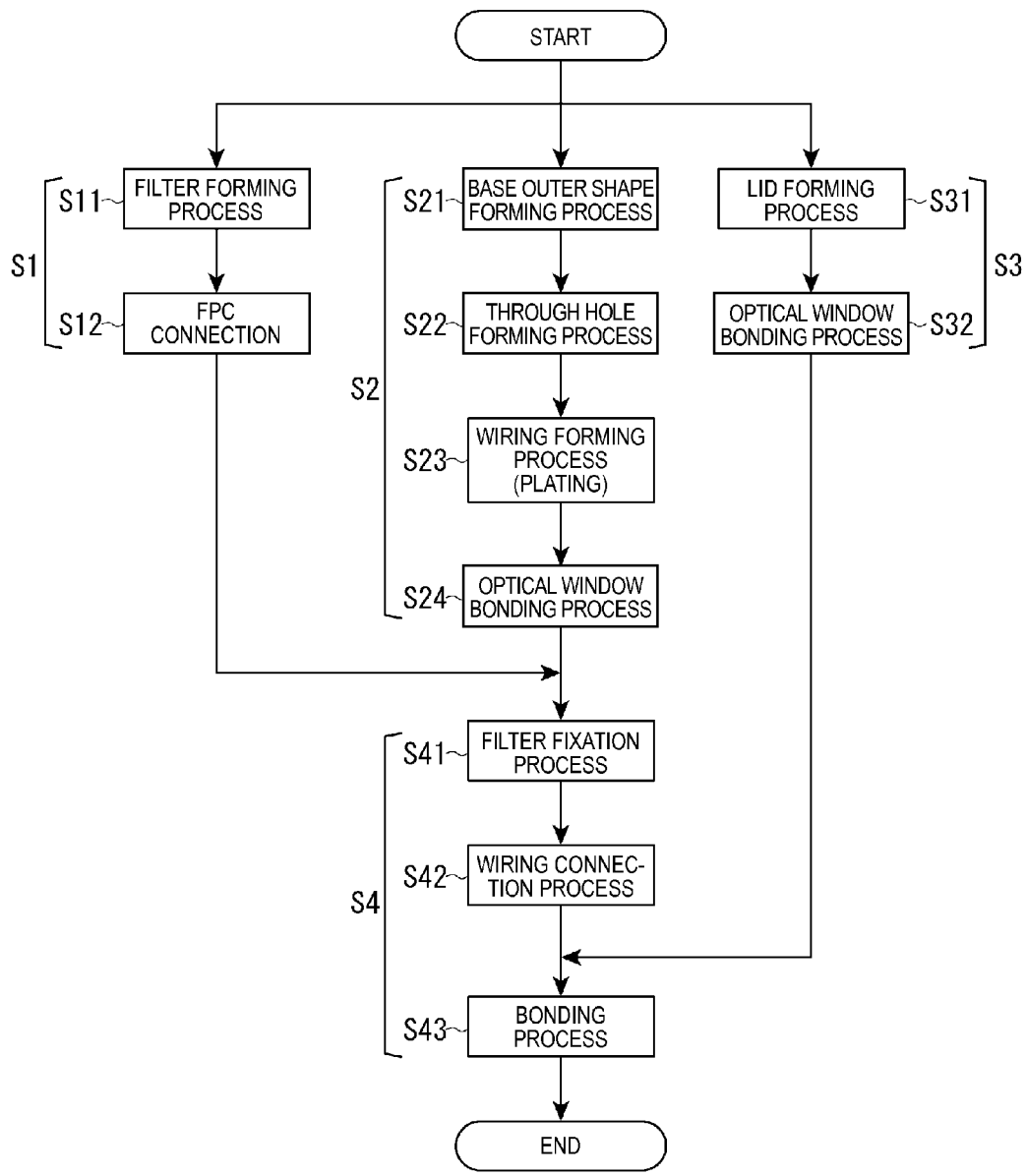
FIG. 7 is a process chart showing a manufacturing process of the optical filter device.

FIG. 7 is a process chart showing the manufacturing process of manufacturing the optical filter device 600.

In the manufacturing process of the optical filter device 600, firstly, there are performed a filter preparation process (S1) for manufacturing the variable wavelength interference filter 5 constituting the optical filter device 600, a base substrate preparation process (S2), and a lid substrate preparation process (S3).

Filter Preparation Process

In the filter preparation process of the step S1, firstly, a filter forming process of manufacturing the variable wavelength interference filter 5 is performed (S11).

In the step S11, the stationary substrate 51 and the movable substrate 52 are formed appropriately using the etching process and so on. Then, with respect to the stationary substrate 51, after depositing the stationary electrode 561 and the stationary extraction electrode 563 thereon, the non-light transmissive member 515 is deposited, and subsequently, the stationary reflecting film 54 is deposited. Further, with respect to the movable substrate 52, after depositing the movable electrode 562, the movable reflecting film 55 is deposited.

Subsequently, by bonding the stationary substrate 51 and the movable substrate 52 to each other via the bonding film 53, the variable wavelength interference filter 5 can be obtained.

Subsequently, an FPC connecting process of connecting the FPCs 615A to the stationary electrode pad 563P and the movable electrode pad 564P of the variable wavelength interference filter 5 obtained in the step S11 is performed (S12). The Ag paste with little gas emission is used for connecting the FPCs 615A and the electrode pads 563P, 564P.

Base Substrate Preparation Process

In the base substrate preparation process of the step S2, firstly, a base outer shape forming process is performed (S21). In the step S21, a pre-calcination substrate formed by laminating sheets as a molded material of a ceramic substrate is appropriately cut to thereby form the shape of the base substrate 610 having the light passage hole 611. Then, by calcining the pre-calcination substrate, the base substrate 610 is formed.

It should be noted that the light passage hole 611 can also be formed by performing the process using a high-power laser such as a YAG laser on the base substrate 610 thus formed by the calcination.

Then, a through hole forming process for providing the through holes 614 to the base substrate 610 is performed (S22). In the step S22, in order to form the fine through holes 614, a laser process using, for example, a YAG laser is performed. Further, the through holes 614 thus formed are filled with the conductive material having a high adhesiveness.

Subsequently, a wiring forming process for providing the internal terminal sections 615 and the external terminal sections 616 to the base substrate 610 is performed (S23).

In the step S23, the plating process using metal such as Ni/Au is performed to thereby form the through holes 614 and the internal terminal sections 615. Further, in the case of bonding the base bonding section 617 and the lid bonding section 624 to each other using the laser welding, the plating with Ni or the like is performed on the base bonding section 617 to thereby form the bonding pattern 617A.

Subsequently, an optical window bonding process for bonding the base-side glass substrate 630 for covering the light passage hole 611 to the base substrate 610 is performed (S24).

In the step S24, firstly, a glass substrate having the length "a" of one side fulfilling the condition of a/d≥1.6 with respect to the hole diameter "d" of the light passage hole 611 is formed as the base-side glass substrate 630. Then, an alignment adjustment is performed so that the planar center of the base-side glass substrate 630 and the planar center of the light passage hole 611 coincide with each other, and then, the base-side glass substrate 630 is bonded to the base substrate 610 by the frit glass bonding process using the frit glass.

Lid Preparation Process

In the lid preparation process of the step S3, firstly, a lid forming process of forming the lid 620 is performed (S31). In the step S31, a press process is performed on a metal substrate formed of kovar or the like to thereby form a lid 620 having the light passage hole 621.

Subsequently, an optical window bonding process for bonding the lid-side glass substrate 640 for covering the light passage hole 621 to the lid 620 is performed (S32).

In the step S32, similarly to the step S24, a glass substrate having the length "a" of one side fulfilling the condition of a/d≥1.6 with respect to the hole diameter "d" of the light passage hole 621 is formed as the lid-side glass substrate 640. Then, an alignment adjustment is performed so that the planar center of the lid-side glass substrate 640 and the planar center of the light passage hole 621 coincide with each other, and then, the lid-side glass substrate 640 is bonded to the lid 620 by the frit glass bonding process using the frit glass.

Device Assembly Process

Then, a device assembly process of bonding the variable wavelength interference filter 5, the base substrate 610, and the lid 620 obtained by the steps S1 through S3 described above to each other to thereby form the optical filter device 600 is performed (S4).

In the step S4, firstly, a filter fixation process of fixing the variable wavelength interference filter 5 to the base substrate 610 is performed (S41). In the step S41, an alignment adjustment is performed so that the planar center point O of the stationary reflecting film 54 and the movable reflecting film 55 coincides with the planar center point O of the light passage hole 611. Then, the substrate outer peripheral portion 525 of the movable substrate 52 is fixed to the base substrate 610 by bonding using, for example, an adhesive.

Subsequently, a wiring connection process is performed (S42). In the step S42, the other ends of the FPCs 615A connected to the variable wavelength interference filter 5 in the step 12 are bonded to the internal terminal sections 615 of the base substrate 610 to thereby connect the internal terminal sections 615 respectively to the stationary electrode pad 563P and the movable electrode pad 564P. In this connection process, it is also preferable to use the Ag paste with little gas emission.

Subsequently, a bonding process for bonding the base substrate 610 and the lid 620 to each other is performed (S43). In the step S43, the base substrate 610 and the lid 620 are made to overlap each other in an environment set to the vacuum atmosphere in, for example, a vacuum chamber device, and are then bonded to each other by laser bonding using, for example, a YAG laser. In such a laser bonding process, since the bonding is performed by locally heating only the bonding area to high temperature, a rise in temperature in the internal space 650 can be suppressed. Therefore, the problem that the reflecting films 54, 55 of the variable wavelength interference filter 5 are deteriorated due to the high temperature can be prevented.

In such a manner as described hereinabove, the optical filter device 600 is manufactured.

Functions and Advantages of Embodiment

In the present embodiment, the optical filter device 600 is provided with the variable wavelength interference filter 5 and the housing 601 for housing the variable wavelength interference filter 5. The housing 601 is provided with the base substrate 610, the lid 620 to be bonded to the base substrate 610, the base-side glass substrate 630 for blocking the light passage hole 611 of the base substrate 610, and the lid-side glass substrate 640 for blocking the light passage hole 621 of the lid 620. Further, the base-side glass substrate 630 is bonded to the base substrate 610 in the area extending from the outer peripheral edge 611A of the light passage hole 611 to the substrate edge 631 of the base-side glass substrate 630. Similarly, the lid-side glass substrate 640 is bonded to the lid 620 in the area extending from the outer peripheral edge 621A of the light passage hole 621 to the substrate edge 641 of the lid-side glass substrate 640.

In such a configuration, it is possible to increase the bonding area and to enhance the bonding strength and the airtightness of the internal space 650 compared to the configuration of, for example, fitting a glass member having a shape corresponding to the light passage hole 611 (the light passage hole 621) into the light passage hole 611 (the light passage hole 621). Therefore, it is possible to prevent foreign matters such as water particles or electrically-charged particles from entering the inside of the optical filter device 600 to thereby prevent the degradation (e.g., the degradation of the resolution) of the optical characteristics of the wavelength interference filter 5 due to such foreign matters.

In the present embodiment, the base-side glass substrate 630 is bonded to the base exterior surface 613 of the base substrate 610, and the lid-side glass substrate 640 is bonded to the lid exterior surface 623 of the lid 620.

Therefore, it is possible to increase the space volume of the internal space 650 to thereby sufficiently provide the housing space for the variable wavelength interference filter 5 compared to the configuration in which, for example, the base-side glass substrate 630 and the lid-side glass substrate 640 are bonded to the interior surfaces of the housing 601. Therefore, it is not necessary to increase the size of the base substrate 610 or the lid 620 in order to, for example, provide the housing space for the variable wavelength interference filter 5, and thus, it is possible to achieve downsizing of the optical filter device 600.

In the present embodiment, the base substrate 610 is provided with the light passage hole 611 through which the light transmitted through the variable wavelength interference filter 5 passes, and the lid 620 is provided with the light passage hole 621 through which the light entering the variable wavelength interference filter 5 passes.

As described above, in the configuration of providing the light passage holes to both the base substrate 610 and the lid 620, the transmissive filter for transmitting the light with the target wavelength emitted by the multiple interferences can be used as the variable wavelength interference filter 5. In this case, since the light with the target wavelength is transmitted toward the opposite side to the entrance side of the incident light, it is possible to avoid such a problem that the incident light is mixed with the transmitted light, and thus high-resolution light with a narrow half bandwidth can be emitted as the light with the target wavelength.

In the present embodiment, the internal space 650 of the housing 601 is kept in the vacuum state. Further, the variable wavelength interference filter 5 is arranged so that the size of the inter-reflecting film gap G1 can be varied by applying voltages to the stationary electrode 561 and the movable electrode 562 to thereby move the movable section 521 toward the stationary substrate 51.

In such a configuration, since the internal space 650 is in the vacuum state, the inter-reflecting film gap G1 is also set to the vacuum state. Therefore, no air resistance acts thereon when moving the movable section 521, and it is possible to improve the response when applying the voltage between the stationary electrode 561 and the movable electrode 562. Therefore, it is possible to promptly set the inter-reflecting film gap G1 to a desired size, and thus prompt processing can be performed when performing a variety of processes such as a measurement process using the optical filter device 600.

In the present embodiment, the light passage holes 611, 621 are formed to have a circular shape and the lid-side glass substrate 640 and the base-side glass substrate 630 are formed to have a square shape in the plan view of the optical filter device 600 viewed from the thickness direction of the base substrate 610. Further, when denoting the hole diameter of the light passage holes 611, 621 as "d," the length of one side of the base-side glass substrate 630 and the lid-side glass substrate 640 as "a," the relationship of a/d≥1.6 is fulfilled.

Further, alignment adjustment is performed on the base-side glass substrate 630 and the lid-side glass substrate 640 so as to have the planar center point O coinciding with the planar center point O of the light passage holes 611, 621, and the base-side glass substrate 630 and the lid-side glass substrate 640 are bonded respectively to the base substrate 610 and the lid 620. In other words, the distance from the substrate edge 631 of the base-side glass substrate 630 to the outer peripheral edge 611A of the light passage hole 611 and the distance from the substrate edge 641 of the lid-side glass substrate 640 to the outer peripheral edge 621A of the light passage hole 621 are set to a dimension equal to or larger than 0.3 d.

By using the base-side glass substrate 630 and the lid-side glass substrate 640 having such dimensions, the deflection of the base-side glass substrate 630 and the lid-side glass substrate 640 due to the stress by the vacuum state can be suppressed to a level not affecting the measurement process. Therefore, the degradation of the resolution of the variable wavelength interference filter 5 can be suppressed, and thus, it is possible to selectively emit the light having the desired target wavelength with accuracy.

In the present embodiment, the internal terminal sections 615 are disposed on the base interior surface 612 of the base substrate 610, and the internal terminal sections 615 are connected to the external terminal sections 616 disposed on the base exterior surface 613 of the base substrate 610. Further, the stationary electrode pad 563P and the movable electrode pad 564P of the variable wavelength interference filter 5 are connected to the respective internal terminal sections 615 corresponding thereto using the FPCs 615A.

In such a configuration, it results that the terminals for applying the voltages to the respective electrodes 561, 562 of the variable wavelength interference filter 5 are formed only on the base exterior surface 613, which is one surface side of the base substrate 610 of the optical filter device 600, and thus the wiring configuration in the case of installing the optical filter device 600 in, for example, an optical module or an electronic apparatus can be simplified, and further, the wiring work thereof also becomes easy.

Further, by applying the voltages respectively to the external terminal sections 616 corresponding to the stationary electrode 561 and the external terminal section 616 corresponding to the movable electrode 562, the size of the inter-reflecting film gap G1 of the variable wavelength interference filter 5 can be changed to the size corresponding to the voltage value due to the electrostatic attractive force, and thus, the light with a desired target wavelength can be emitted using the variable wavelength interference filter 5.

In the present embodiment, the base substrate 610 is provided with the through holes 614, and the through holes 614 are filled with the conductive member for connecting the internal terminal sections 615 and the external terminal sections 616 to each other. By filling the gap of the through holes 614 with the conductive member as described above, it is possible to keep the airtightness of the internal space 650, and at the same time to electrically connect the internal terminal sections 615 disposed on the base interior surface 612 of the base substrate 610 and the external terminal sections 616 disposed on the base exterior surface 613 to each other. Further, since the conductive member of the through holes 614 has direct contact with the internal terminal sections 615 and the external terminal sections 616 to thereby connect them to each other, the wiring reliability can be enhanced.

In the present embodiment, the non-light transmissive member 515 having a ring-like shape is disposed on the light entrance surface 51A of the stationary substrate 51 as a surface through which the light enters the variable wavelength interference filter 5, and the effective range of making the light enter the stationary reflecting film 54 and the movable reflecting film 55 is determined by the inner diameter of the ring of the non-light transmissive member 515. In other words, the non-light transmissive member 515 functions as an aperture.

In general, in the case of forming the outer shape of the stationary substrate 51 and the movable substrate 52 by processing using the etching process, a curved part is formed along the periphery of the etched portion due to the influence of the side etching. If the light enters such a curved part, refraction and reflection occur, which causes the stray light. Such stray light might be transmitted while being mixed with the light having the target wavelength emitted due to the multiple interferences by the stationary reflecting film 54 and the movable reflecting film 55 in some cases, and in such cases, degradation of the optical characteristics such as degradation in resolution in the variable wavelength interference filter 5 is caused.

In contrast thereto, in the present embodiment, since the non-light transmissive member 515 as an aperture defines the entrance range of the light, entrance of the light to the curved part described above can be prevented to thereby prevent the degradation of the optical characteristics due to the stray light.

Further, by adopting the configuration of providing the non-light transmissive member 515 to the stationary substrate 51, the alignment adjustment can accurately be performed on the stationary reflecting film 54 and the movable reflecting film 55, and the effective diameter thereof functioning as the aperture can accurately be set compared to the configuration of, for example, providing the non-light transmissive member 515 to the lid-side glass substrate 640.

Second Embodiment

Next, a second embodiment of the invention will be explained with reference to the accompanying drawings.

In the second embodiment, a colorimetric sensor 3 as an optical module incorporating the optical filter device 600 according to the first embodiment described above, and a colorimetric device 1 as an electronic apparatus incorporating the optical filter device 600 will be explained.

1. Schematic Configuration of Colorimetric Device

Figure 8:
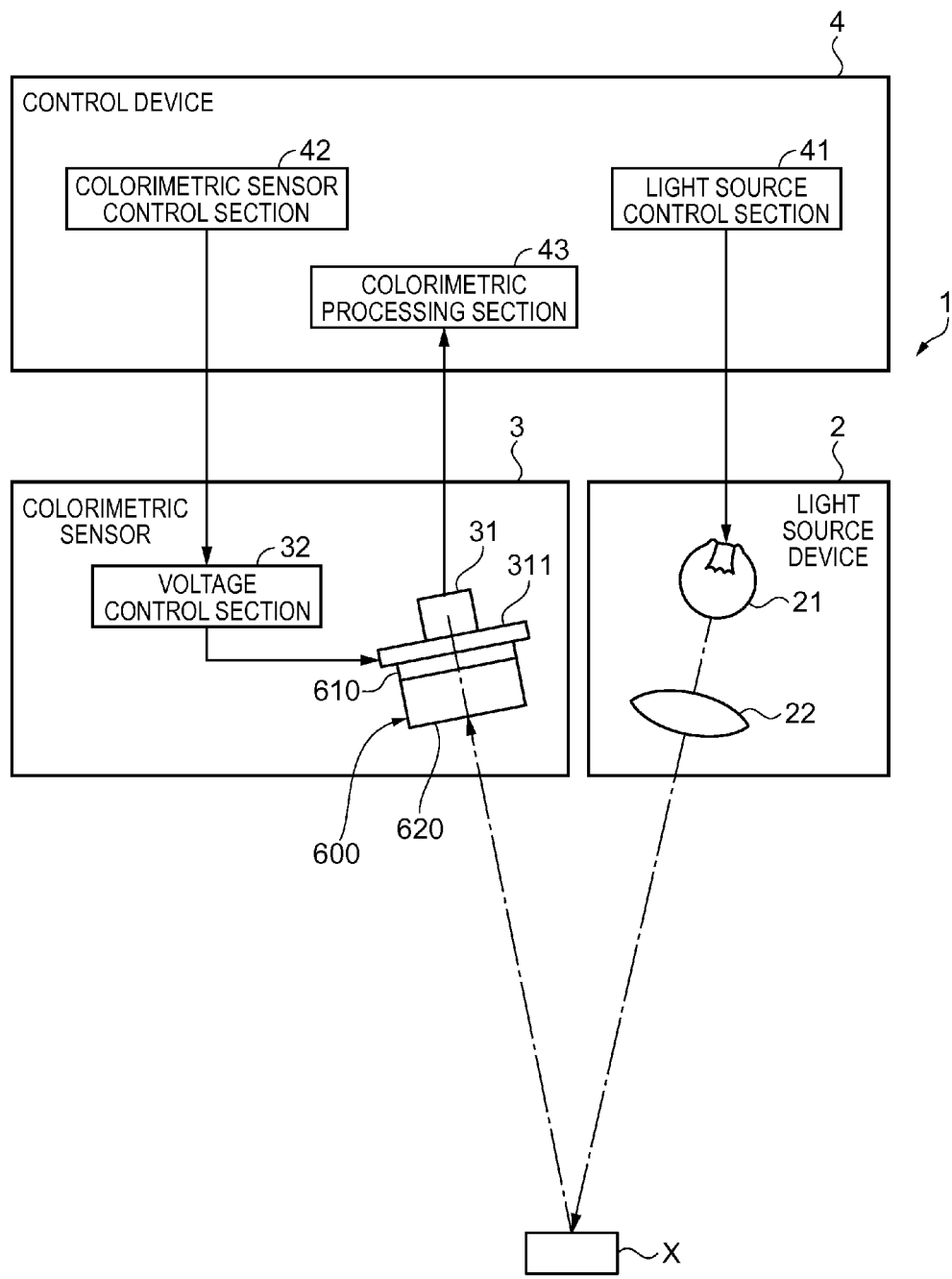
FIG. 8 is a block diagram showing a schematic configuration of a colorimetric device according to a second embodiment of the invention.

FIG. 8 is a block diagram showing a schematic configuration of a colorimetric device 1 according to the second embodiment.

The colorimetric device 1 is an example of an electronic apparatus. As shown in FIG. 8, the colorimetric device 1 is provided with a light source device 2 for emitting light to a test object X, the colorimetric sensor 3, and a control device 4 for controlling an overall operation of the colorimetric device 1. Further, the colorimetric device 1 is a device for making the light, which is emitted from the light source device 2, be reflected by the test object X, receiving the test target light thus reflected using the colorimetric sensor 3, and analyzing and then measuring the chromaticity of the test target light, namely the color of the test object X, based on the detection signal output from the colorimetric sensor 3.

2. Configuration of Light Source Device

The light source device 2 is provided with a light source 21 and a plurality of lenses 22 (one of the lenses is shown alone in FIG. 8), and emits a white light to the test object X. Further, it is possible for the plurality of lenses 22 to include a collimator lens, and in this case, the light source device 2 converts the white light emitted from the light source 21 into a parallel light with the collimator lens, and emits it from the projection lens not shown toward the test object X. It should be noted that although in the present embodiment the colorimetric device 1 provided with the light source device 2 is described as an example, in the case in which, for example, the test object X is a light emitting member such as a liquid crystal panel, it is also possible to adopt a configuration not provided with the light source device 2.

3. Configuration of Colorimetric Sensor

The colorimetric sensor 3 is an example of an optical module, and is provided with the optical filter device 600 according to the first embodiment. As shown in FIG. 8, the colorimetric sensor 3 is provided with the optical filter device 600, a detection section 31 for receiving the light transmitted through the variable wavelength interference filter 5 of the optical filter device 600, and a voltage control section 32 for varying the wavelength of the light to be transmitted through the variable wavelength interference filter 5.

Further, the colorimetric sensor 3 is provided with an entrance optical lens (not shown) disposed at a position opposed to the variable wavelength interference filter 5, the entrance optical lens guiding the reflected light (the test target light), which has been reflected by the test object X, into the inside thereof. Further, the colorimetric sensor 3 disperses the light with a predetermined wavelength out of the test target light having entered from the entrance optical lens using the variable wavelength interference filter 5 in the optical filter device 600, and then receives the light thus dispersed using the detection section 31.

The detection section 31 is composed of a plurality of photoelectric conversion elements, and generates an electric signal corresponding to the received light intensity. Here, the detection section 31 is connected to the control device 4 via, for example, a circuit board 311, and outputs the electric signal thus generated to the control device 4 as a light reception signal.

Further, the external terminal sections 616 formed on the base exterior surface 613 of the base substrate 610 are connected to the circuit board 311, and are connected to the voltage control section 32 via a circuit provided to the circuit board 311.

In such a configuration, the optical filter device 600 and the detection section 31 can integrally be configured via the circuit board 311, and thus the configuration of the colorimetric sensor 3 can be simplified.

The voltage control section 32 is connected to the external terminal sections 616 of the optical filter device 600 via the circuit board 311. Further, the voltage control section 32 applies a predetermined step voltage between the stationary electrode pad 563P and the movable electrode pad 564P based on a control signal input from the control device 4 to thereby drive the electrostatic actuator 56. Thus, the electrostatic attractive force is generated in the inter-electrode gap G2, the holding section 522 is deflected to thereby displace the movable section 521 toward the stationary substrate 51, and thus it becomes possible to set the inter-reflecting film gap G1 to the desired size.

4. Configuration of Control Device

The control device 4 controls an overall operation of the colorimetric device 1.

As the control device 4, a general-purpose personal computer, a handheld terminal, a colorimetry-dedicated computer, and so on can be used.

Further, as shown in FIG. 8, the control device 4 is configured including a light source control section 41, a colorimetric sensor control section 42, a colorimetric processing section 43, and so on.

The light source control section 41 is connected to the light source device 2. Further, the light source control section 41 outputs a predetermined control signal to the light source device 2 based on, for example, a setting input by the user to thereby make the light source device 2 emit a white light with a predetermined brightness.

The colorimetric sensor control section 42 is connected to the colorimetric sensor 3. Further, the colorimetric sensor control section 42 sets the wavelength of the light to be received by the colorimetric sensor 3 based on, for example, the setting input by the user, and then outputs the control signal, which instructs the detection of the intensity of the received light having the wavelength thus set, to the colorimetric sensor 3. Thus, the voltage control section 32 of the colorimetric sensor 3 sets the voltage to be applied to the electrostatic actuator 56 based on the control signal so as to transmit only the light having the wavelength desired by the user.

The colorimetric processing section 43 analyzes the chromaticity of the test object X based on the light reception intensity detected by the detection section 31.

5. Functions and Advantages of Embodiment

The colorimetric device 1 according to the present embodiment is provided with the optical filter device 600 according to the first embodiment described above. As described above, since the optical filter device 600 has the superior airtightness of the internal space 650, and thus there is no invasion of foreign matters such as water particles, it is possible to prevent the change in optical characteristics of the variable wavelength interference filter 5 due to such foreign matters. Therefore, also in the colorimetric sensor 3, light having the target wavelength emitted at high resolution can be detected with the detection section 31, and thus the correct light intensity with respect to the light having the desired target wavelength can be detected. Thus, it is possible for the colorimetric device 1 to perform the accurate color analysis of the test object X.

Further, the detection section 31 is disposed so as to be opposed to the base substrate 610, and the detection section 31 and the external terminal sections 616 disposed on the base exterior surface 613 of the base substrate 610 are connected to the single circuit board 311. In other words, the base substrate 610 of the optical filter device 600 is disposed on the light exit side, and can therefore be disposed in vicinity to the detection section 31 for detecting the light emitted from the optical filter device 600. Therefore, as described above, by providing the wiring to the single circuit board 311, the wiring structure can be simplified, and the number of boards can also be reduced.

Further, it is also possible to dispose the voltage control section 32 on the circuit board 311, and in this case, further simplification of the configuration can be achieved.

Modified Examples

It should be noted that the invention is not limited to the embodiments described above, but includes modifications, improvements, and so on within a range where the advantages of the invention can be achieved.

For example, although in the first embodiment the optical filter device 600 having the internal space 650 kept in the vacuum state is manufactured by bonding the base substrate 610 and the lid 620 to each other in a vacuum, the invention is not limited thereto.

Figure 9:
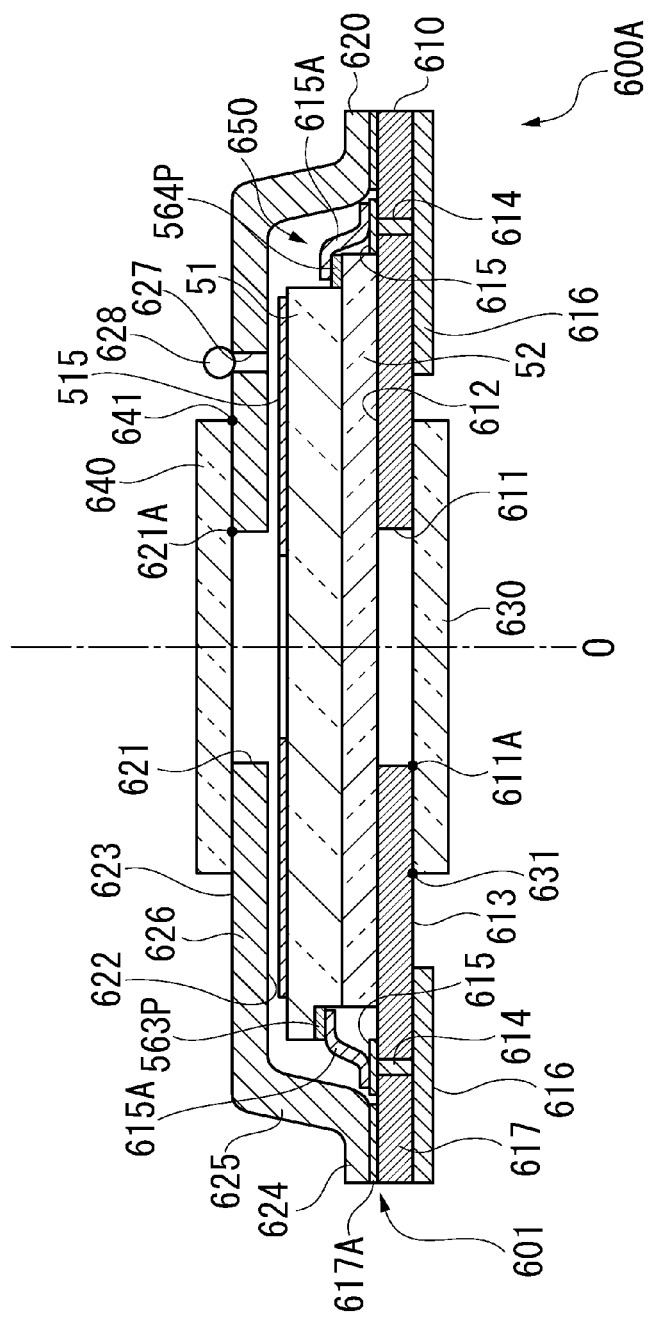
FIG. 9 is a cross-sectional view showing a schematic configuration of an optical filter device according to a modified example.

FIG. 9 is a cross-sectional view showing an optical filter device according to a modified example.

As shown in FIG. 9, the optical filter device 600A has a hole 627 in a part of the lid 620, the hole 627 for allowing the internal space 650 and the external space to communicate with each other. The hole 627 is formed so that the shape of at least the part of the hole adjacent to the base exterior surface 613 is circular. Further, the hole 627 is sealed by installing a metal ball 628 (a seal member) from the base exterior surface 613 side. In the seal by the metal ball 628, it is preferable to fit the metal ball 628 into the hole 627, and then heat the metal ball 628 to a high temperature inside the hole 627 to thereby weld it to the interior wall of the hole 627.

In such an optical filter device 600A, it becomes possible to set the internal space 650 to the vacuum state after bonding the base substrate 610 and the lid 620 to each other. Specifically, in the optical filter device 600 according to the first embodiment, as shown in FIG. 7, the base substrate 610 and the lid 620 are bonded to each other by laser welding using a high-power laser such as a YAG laser in the step S43. However, depending on the materials of the base substrate 610 and the lid 620, the manufacturing environment, and so on, bonding by a soldering process or a brazing process using brazing metal is performed, for example, in the atmospheric pressure in some cases.

In such cases, according to the modified example, it is possible to create the vacuum state by evacuating the air in the internal space 650 through the hole 627 of the lid 620 after bonding the base substrate 610 and the lid 620 to each other, and then keep the vacuum state by installing the metal ball 628 to thereby seal the internal space 650.

Further, although in the modified example described above the configuration of providing the hole 627 in the lid 620 is shown, it is also possible to adopt a configuration of providing the hole 627 in the base substrate 610, or a configuration of providing holes 627 in both the base substrate 610 and the lid 620. Further, the number of holes 627 is not limited to one, but a configuration of providing a plurality of holes 627 can also be adopted. For example, it is also possible to adopt a configuration of providing a plurality of holes 627 in each of the base substrate 610 and the lid 620. Also in this case, by sealing each of the holes 627 with the metal ball 628, the airtightness of the internal space 650 can be assured.

Further, although in the first embodiment described above, there is described an example of the optical filter device 600 incorporating the variable wavelength interference filter 5 capable of varying the size of the inter-reflecting film gap G1 due to the electrostatic attractive force by applying the voltages to the stationary electrode 561 and the movable electrode 562, the invention is not limited thereto. It is also possible to adopt a configuration of, for example, using a dielectric actuator disposing a first dielectric coil instead of the stationary electrode 561, and disposing a second dielectric coil or a permanent magnet instead of the movable electrode 562 as a gap changing section for changing the inter-reflecting film gap G1.

Further, it is also possible to adopt a configuration of using a piezoelectric actuator instead of the electrostatic actuator 56. In this case, for example, a lower electrode layer, a piezoelectric film, and an upper electrode layer are disposed on the holding section 522 in a stacked manner, and the voltage applied between the lower electrode layer and the upper electrode layer is varied as an input value, and thus the piezoelectric film is expanded or contracted to thereby make it possible to deflect the holding section 522.

Further, although the variable wavelength interference filter 5 is exemplified as the interference filter housed in the internal space 650, it is also possible to adopt, for example, an interference filter having the dimension of the inter-reflecting film gap G1 fixed. In this case, it is not necessary to form the holding section 522 for allowing the movable section 521 to be displaced, the electrode arrangement groove 511 for disposing the stationary electrode 561, and so on by etching, and thus the configuration of the interference filter can be simplified. Further, since the dimension of the inter-reflecting film gap G1 is fixed, the problem in response does not arise, it is not required to keep the internal space 650 vacuum, and thus, simplification of the configuration and the enhancement of productivity can be achieved. It should be noted that also in this case, if the optical filter device 600 is used in the place with a large temperature variation, for example, there is a possibility that the base-side glass substrate 630 and the lid-side glass substrate 640 are deflected due to the stress caused by the expansion of the air in the internal space 650. Therefore, even in the case of using such an interference filter, it is preferable to keep the internal space 650 in the vacuum state or a reduced-pressure state.

Further, although there is shown the configuration in which the lid 620 is provided with the lid bonding section 624, the sidewall section 625, and the top surface section 626, and the top surface section 626 is parallel to the base substrate 610, the invention is not limited thereto. As the shape of the lid 620, any shape can be adopted providing the internal space 650 capable of housing the variable wavelength interference filter 5 can be formed between the lid 620 and the base substrate 610, and for example, the top surface section 626 can be formed to have a curved shape. It should be noted that in this case it is possible that the manufacturing process becomes complicated. For example, it is desired that the lid-side glass substrate 640 to be bonded to the lid 620 is formed to have the curved shape in accordance with the lid 620 in order to keep the airtightness of the internal space 650, and at the same time, only the part blocking the light passage hole 621 is formed to have a flat shape so as not to cause refraction. Therefore, it is preferable to use the lid 620 having the top surface section 626 parallel to the base substrate 610 as in the first embodiment described above.

Although in the first embodiment described above, there is shown the example in which the base-side glass substrate 630 and the lid-side glass substrate 640 are bonded to the exterior surface of the housing 601, namely the base exterior surface 613 of the base substrate 610 and the lid exterior surface 623 of the lid 620, the invention is not limited thereto. For example, it is also possible to adopt a configuration in which the glass substrates are bonded to the internal space 650 side of the housing 601.

Further, in the case of housing a reflective filter, which reflects the light on which the multiple interferences is performed by the first reflecting film and the second reflecting film, in the internal space 650 as the interference filter, it is also possible to adopt a configuration in which the light passage hole 611 and the base-side glass substrate 630 are not provided.

In this case, by adopting a configuration of separating the incident light to the optical filter device 600 and the outgoing light emitted from the optical filter device 600 by disposing, for example, a beam splitter so as to be opposed to the light passage hole 621 of the optical filter device 600, it is possible to make the detection section detect the outgoing light thus separated.

Although in the first embodiment described above, there is exemplified the configuration of connecting the internal terminal sections 615 and the external terminal sections 616 to each other via the conductive members disposed inside the through holes 614 provided to the base substrate 610, the invention is not limited thereto. It is also possible to adopt a configuration in which a terminal having a rod-like shape is pressed into each of the through holes 614 of the base substrate 610, and the tip portions of the terminals are connected respectively to the stationary electrode pad 563P, the movable electrode pad 564P, and so on.

Although in the first embodiment described above, the stationary electrode 561 and the movable electrode 562 (and the electrode pads 563P, 564P connected to these electrodes 561, 562) constituting the electrostatic actuator are exemplified as an electrode section provided to the variable wavelength interference filter 5, the invention is not limited thereto.

As another example of the electrodes, there can be cited, for example, a capacitance detection electrode for measuring the dimension of the inter-reflecting film gap G1 based on the variation in charge retaining amount of the stationary reflecting film 54 and the movable reflecting film 55, and a charge removing electrode for releasing the charges retained in the substrates 51, 52, the stationary reflecting film 54, and the movable reflecting film 55 to thereby remove the Coulomb force between the substrates. In such cases, an extraction electrode extracted from the capacitance detection electrode or the charge removing electrode described above is disposed on the first electrical installation surface 514 and the second electrical installation surface 524. Further, even in the case in which the plurality of electrodes is disposed as described above, by bonding, for example, the FPC 615A to the first electrical installation surface 514, the wiring connection can easily be performed without performing a separate connection work on each of the electrodes in, for example, the step S12 in FIG. 7.

Although in the first embodiment described above there is adopted the configuration of providing the non-light transmissive member 515 to the light entrance surface of the stationary substrate 51, it is also possible to adopt a configuration of, for example, providing the non-light transmissive member 515 to the lid-side glass substrate 640 as the transmissive substrate on the entrance side.

Further, although in the first embodiment described above there is exemplified the optical filter device 600 for making the variable wavelength interference filter 5 perform the multiple interferences on the light input from the lid 620 side, and emitting the light, which has been transmitted through the variable wavelength interference filter 5, from the base-side glass substrate 630, it is also possible to adopt a configuration of, for example, inputting the light from the base substrate 610 side. In this case, it is also possible to provide the non-light transmissive member made to function as an aperture to the movable substrate 52, or to adopt a configuration of, for example, fixing the stationary substrate 51 provided with the non-light transmissive member to the base substrate 610.

Further, although the colorimetric device 1 is exemplified in the second embodiment as an electronic apparatus, the optical filter device, the optical module, and the electronic apparatus can be used in a variety of fields besides the above.

For example, they can be used as an optical base system for detecting presence of a specific substance. As such a system, there can be cited, for example, an in-car gas leak detector adopting a spectroscopic measurement method using the variable wavelength interference filter and detecting a specific gas with high sensitivity, and a gas detection device such as an optoacoustic noble-gas detector for breath-testing.

An example of such a gas detection device will hereinafter be explained with reference to the accompanying drawings.

Figure 10:
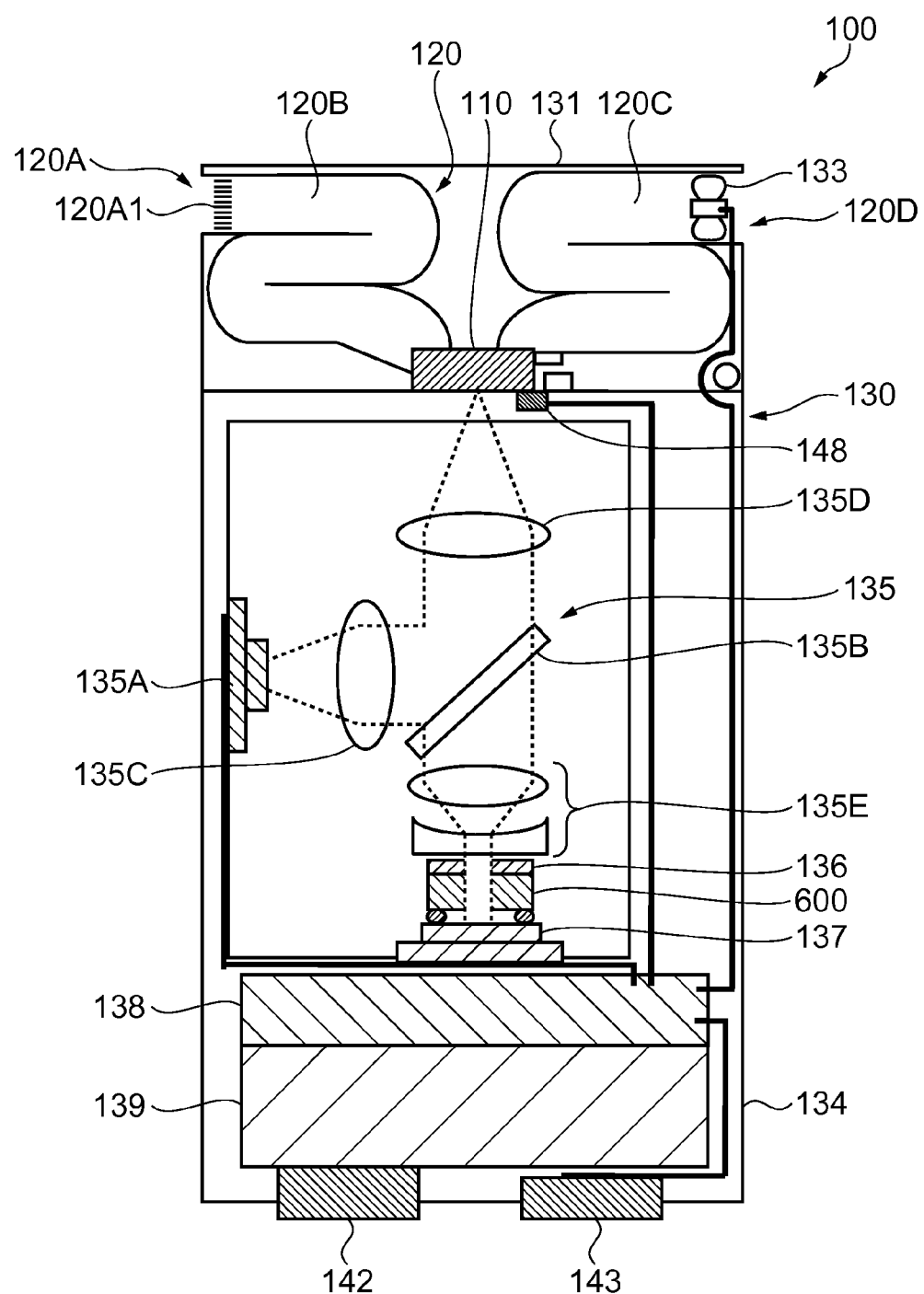
FIG. 10 is a schematic diagram showing a gas detection device equipped with the optical filter device according to an embodiment of the invention.

FIG. 10 is a schematic diagram showing an example of a gas detection device provided with the variable wavelength interference filter.

Figure 11:
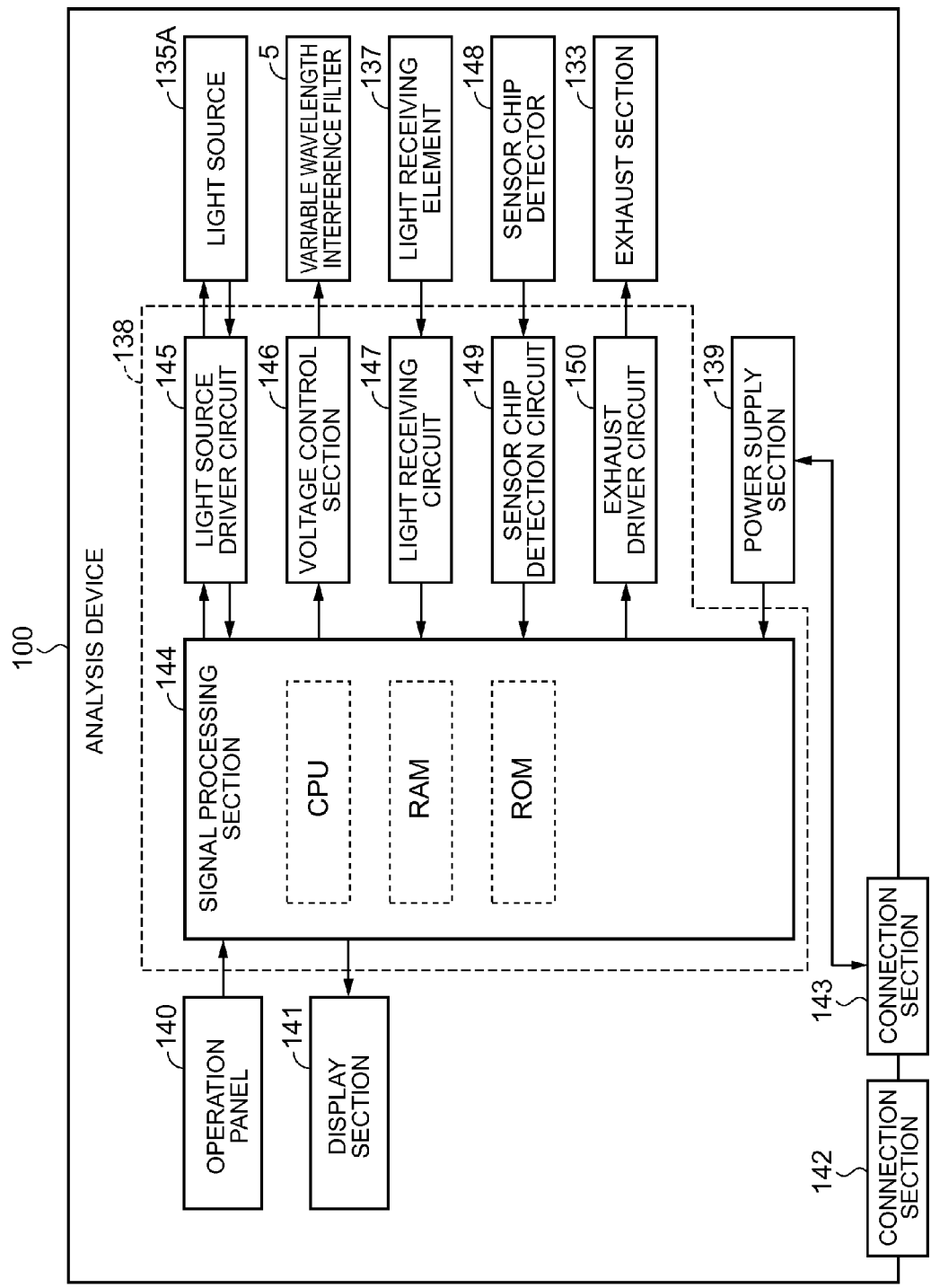
FIG. 11 is a block diagram showing a configuration of a control system of the gas detection device shown in FIG. 10.

FIG. 11 is a block diagram showing a configuration of the control system of the gas detection device shown in FIG. 10.

As shown in FIG. 10, the gas detection device 100 is configured including a sensor chip 110, a channel 120 provided with a suction port 120A, a suction channel 120B, an exhaust channel 120C, and an exhaust port 120D, and a main body section 130.

The main body section 130 is composed of a detection device including a sensor section cover 131 having an opening to which the channel 120 is detachably attached, an exhaust section 133, a housing 134, an optical section 135, a filter 136, the optical filter device 600, a light receiving element 137 (a detection section), and so on, a control section 138 for processing the signal thus detected and controlling the detection section, a power supply section 139 for supplying electrical power, and so on. Further, the optical section 135 is composed of a light source 135A for emitting light, a beam splitter 135B for reflecting the light, which is input from the light source 135A, toward the sensor chip 110, and transmitting the light, which is input from the sensor chip, toward the light receiving element 137, and lenses 135C, 135D, and 135E.

Further, as shown in FIG. 11, on the surface of the gas detection device 100, there are disposed an operation panel 140, a display section 141, a connection section 142 for an interface with the outside, and a power supply section 139. In the case in which the power supply section 139 is a secondary cell, a connection section 143 for the battery charge can also be provided.

Further, as shown in FIG. 11, the control section 138 of the gas detection device 100 is provided with a signal processing section 144 composed of a CPU and so on, a light source driver circuit 145 for controlling the light source 135A, a voltage control section 146 for controlling the variable wavelength interference filter 5 of the optical filter device 600, a light receiving circuit 147 for receiving a signal from the light receiving element 137, a sensor chip detection circuit 149 for receiving a signal from a sensor chip detector 148 for reading a code of a sensor chip 110 and detecting presence or absence of the sensor chip 110, an exhaust driver circuit 150 for controlling the exhaust section 133, and so on.

Then, an operation of the gas detection device 100 described above will hereinafter be explained.

The sensor chip detector 148 is disposed in the sensor section cover 131 in the upper part of the main body section 130, and the sensor chip detector 148 detects presence or absence of the sensor chip 110. When detecting the detection signal from the sensor chip detector 148, the signal processing section 144 determines that it is the condition in which the sensor chip 110 is attached, and outputs a display signal for displaying the fact that the detection operation can be performed to the display section 141.

Then, if, for example, the user operates the operation panel 140, and the operation panel 140 outputs an instruction signal indicating that the detection process will be started to the signal processing section 144, the signal processing section 144 firstly outputs the signal for operating the light source to the light source driver circuit 145 to thereby operate the light source 135A. When the light source 135A is driven, the light source 135A emits a stable laser beam, which has a single wavelength and is a linearly polarized light. Further, the light source 135A incorporates a temperature sensor and a light intensity sensor, and the information thereof is output to the signal processing section 144. Then, if the signal processing section 144 determines that the light source 135A is operating stably based on the temperature and the light intensity input from the light source 135A, the signal processing section 144 controls the exhaust driver circuit 150 to operate the exhaust section 133. Thus, the gaseous sample including the target material (the gas molecule) to be detected is guided from the suction port 120A to the suction channel 120B, the inside of the sensor chip 110, the exhaust channel 120C, and the exhaust port 120D. It should be noted that the suction port 120A is provided with a dust filter 120A1, and relatively large dust, some water vapor, and so on are removed.

Further, the sensor chip 110 is a sensor incorporating a plurality of sets of metal nano-structures, and using localized surface plasmon resonance. In such a sensor chip 110, an enhanced electric field is formed between the metal nano-structures due to the laser beam, and when the gas molecules enter the enhanced electric field, the Raman scattered light including the information of the molecular vibration and the Rayleigh scattered light are generated.

The Rayleigh scattered light and the Raman scattered light pass through the optical section 135 and then enter the filter 136, and the Rayleigh scattered light is separated by the filter 136, and the Raman scattered light enters the optical filter device 600. Then, the signal processing section 144 controls the voltage control section 146 to control the voltage to be applied to the variable wavelength interference filter 5 of the optical filter device 600 to thereby make the variable wavelength interference filter 5 of the optical filter device 600 disperse the Raman scattered light corresponding to the gas molecules to be the detection object. After then, if the light thus dispersed is received by the light receiving element 137, the light reception signal corresponding to the received light intensity is output to the signal processing section 144 via the light receiving circuit 147.

The signal processing section 144 compares the spectrum data of the Raman scattered light corresponding to the gas molecule to be the detection object obtained as described above and the data stored in the ROM with each other to thereby determine whether or not it is the target gas molecule, and thus the substance is identified. Further, the signal processing section 144 makes the display section 141 display the result information, or outputs it from the connection section 142 to the outside.

It should be noted that although in FIGS. 10 and 11 the gas detection device 100 for dispersing the Raman scattered light with the variable wavelength interference filter 5 of the optical filter device 600, and performing the gas detection based on the Raman scattered light thus dispersed is cited as an example, it is also possible to use the device as a gas detection device for identifying the gas type by detecting the absorbance unique to the gas. In this case, the gas is made to flow into the sensor, and the gas sensor for detecting the light absorbed by the gas in the incident light is used as an optical module. Further, the gas detection device for analyzing and determining the gas flowing into the sensor using such a gas sensor is cited as an example of an electronic apparatus. It is possible to detect the component of the gas using the variable wavelength interference filter also in such a configuration.

Further, as the system for detecting the presence of the specific substance, besides the gas detection described above, there can be cited a substance component analysis device such as a non-invasive measurement device of sugar group using near-infrared dispersion or a non-invasive measurement device of the information of food, biological object, or mineral.

Hereinafter, as an example of the substance component analysis device described above, a food analysis device will be explained.

Figure 12:
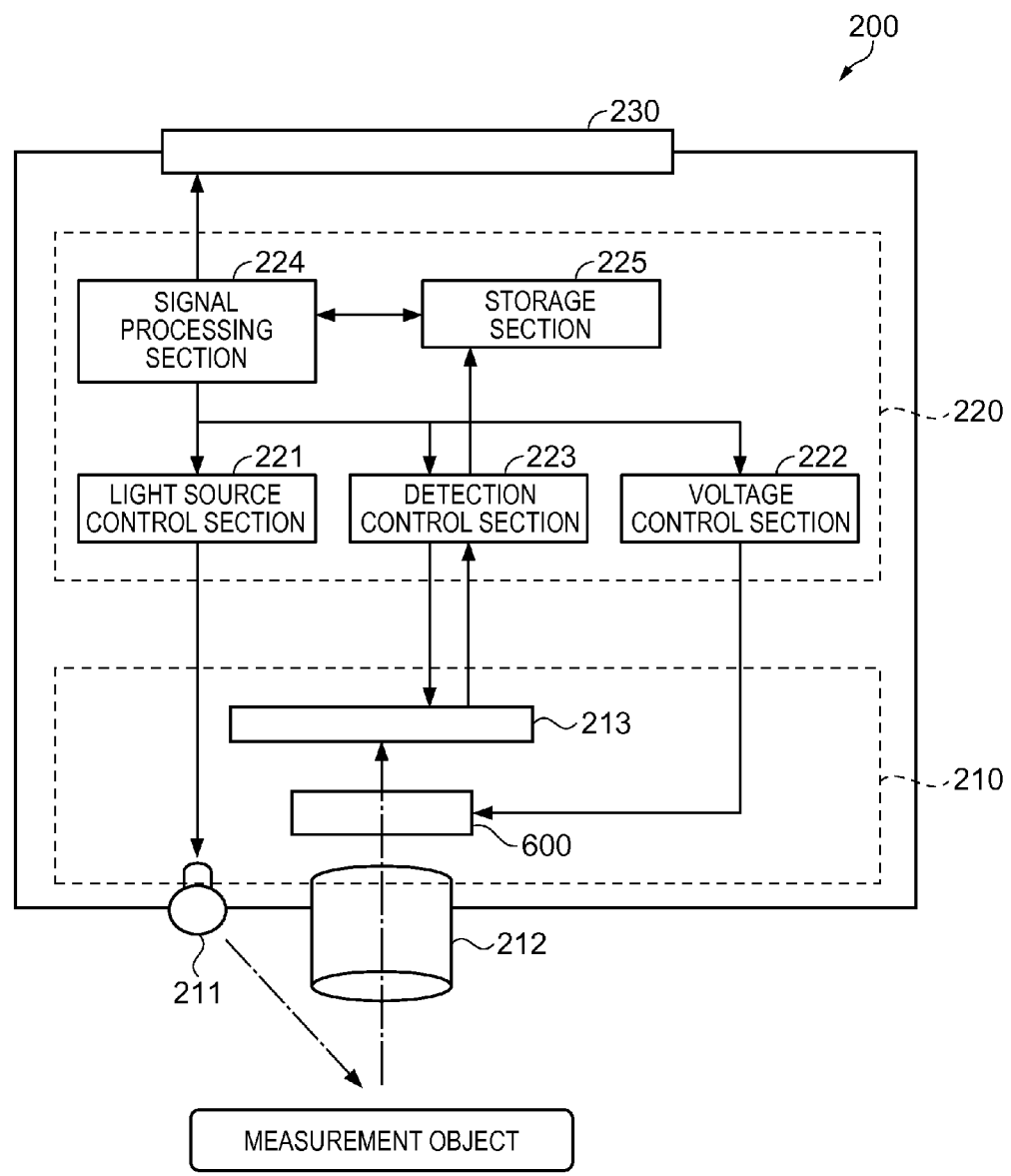
FIG. 12 is a diagram showing a schematic configuration of a food analysis device equipped with the optical filter device according to an embodiment of the invention.

FIG. 12 is a diagram showing a schematic configuration of the food analysis device as an example of the electronic apparatus using the optical filter device 600.

As shown in FIG. 12, the food analysis device 200 is provided with a detector 210 (the optical module), a control section 220, and a display section 230. The detector 210 is provided with a light source 211 for emitting light, an image pickup lens 212 to which the light from a measurement object is introduced, the optical filter device 600 for dispersing the light thus introduced from the image pickup lens 212, and an image pickup section 213 (a detection section) for detecting the light thus dispersed.

Further, the control section 220 is provided with a light source control section 221 for performing lighting/extinction control of the light source 211 and brightness control when lighting the light source 211, a voltage control section 222 for controlling the variable wavelength interference filter 5 of the optical filter device 600, a detection control section 223 for controlling the image pickup section 213 and obtaining a spectral image picked up by the image pickup section 213, a signal processing section 224, and a storage section 225.

In the food analysis device 200, when the system is started up, the light source control section 221 controls the light source 211, and the light source 211 irradiates the measurement object with the light. Then, the light reflected by the measurement object passes through the image pickup lens 212 and then enters the optical filter device 600. The voltage with which the variable wavelength interference 5 of the optical filter device 600 can disperse the light into desired wavelengths is applied to the variable wavelength interference filter 5 under the control of the voltage control section 222, and the light thus dispersed is picked up by the image pickup section 213 formed of, for example, a CCD camera. Further, the light thus picked up is stored in the storage section 225 as the spectral image. Further, the signal processing section 224 controls the voltage control section 222 to vary the voltage value to be applied to the variable wavelength interference filter 5 to thereby obtain the spectral image corresponding to each wavelength.

Then, the signal processing section 224 performs an arithmetic process on the data of each pixel in each of the images stored in the storage section 225 to thereby obtain the spectrum in each pixel. Further, the storage section 225 stores, for example, information related to component of food corresponding to the spectrum, and the signal processing section 224 analyzes the data of the spectrum thus obtained based on the information related to the food stored in the storage section 225, and then obtains the food component included in the detection object and the content thereof. Further, the calorie of the food, the freshness thereof, and so on can also be calculated based on the food component and the content thus obtained. Further, by analyzing the spectral distribution in the image, it is possible to perform extraction of the portion with low freshness in the food as a test object, and further, it is also possible to perform detection of a foreign matter included in the food.

Then, the signal processing section 224 performs a process of making the display section 230 display the information of the components, the contents, the calorie, the freshness, and so on of the food as the test object obtained as described above.

Further, FIG. 12 shows an example of the food analysis device 200. It is also possible to use substantially the same configuration as the non-invasive measurement device of other information as described above. For example, it can be used as a biological analysis device for analyzing a biological component such as measurement and analysis of a biological fluid such as blood. If a device of detecting ethyl alcohol is provided as a device of measuring the biological fluid component such as blood as an example of such a biological analysis device, the device can be used as a device for detecting the influence of alcohol to the driver to thereby prevent driving under the influence of alcohol. Further, it can also be used as an electronic endoscopic system equipped with such a biological analysis device.

Further, it can also be used as a mineral analysis device for performing component analysis of minerals.

Further, the variable wavelength interference filter, the optical module, and the electronic apparatus can be applied to the following devices.

For example, it is also possible to transmit data with the light having each of the wavelengths by temporally varying the intensity of the light having each of the wavelengths, and in this case, it is possible to extract the data transmitted with the light having a specific wavelength by dispersing the light having the specific wavelength using the variable wavelength interference filter provided to the optical module, and then making the light receiving section receive the light. Therefore, by processing the data of the light having each of the wavelengths using the electronic apparatus equipped with such a data extracting optical module, it is also possible to perform optical communication.

Further, the electronic apparatus can be applied to a spectroscopic camera for picking up the spectral image and a spectroscopic analysis device by dispersing the light with the variable wavelength interference filter. As an example of such a spectroscopic camera, an infrared camera incorporating the variable wavelength interference filter can be cited.

Figure 13:
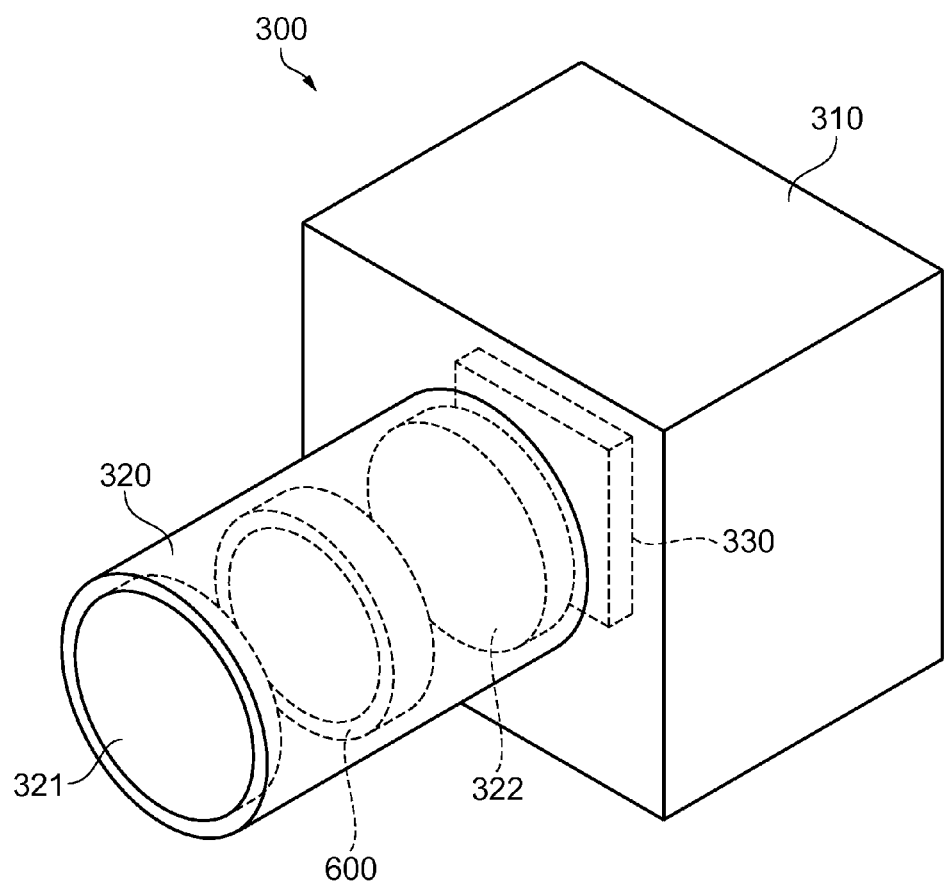
FIG. 13 is a schematic diagram showing a schematic configuration of a spectroscopic camera equipped with the optical filter device according to an embodiment of the invention.

FIG. 13 is a schematic diagram showing a schematic configuration of the spectroscopic camera. As shown in FIG. 13, the spectroscopic camera 300 is provided with a camera main body 310, an image pickup lens unit 320, and an image pickup section 330 (a detection section).

The camera main boy 310 is a part which is gripped and operated by the user.

The image pickup lens unit 320 is provided to the camera main body 310, and guides the image light input thereto to the image pickup section 330. Further, as shown in FIG. 13, the image pickup lens unit 320 is configured including an objective lens 321, an imaging lens 322, and the optical filter device 600 disposed between these lenses.

The image pickup section 330 is formed of a light receiving element, and picks up the image light guided by the image pickup lens unit 320.

In such a spectroscopic camera 300, by transmitting the light with the wavelength to be the imaging object using the variable wavelength interference filter 5 of the optical filter device 600, the spectral image of the light with a desired wavelength can be picked up.

Further, the variable wavelength interference filter can be used as a band-pass filter, and can also be used as, for example, an optical laser device for dispersing and transmitting only the light with a narrow band centered on a predetermined wavelength out of the light in a predetermined wavelength band emitted by the light emitting element using the variable wavelength interference filter.

Further, the variable wavelength interference filter can be used as a biometric authentication device, and can be applied to, for example, an authentication device of blood vessels, a fingerprint, a retina, an iris, and so on using the light in a near infrared range or a visible range.

Further, the optical module and the electronic apparatus can be used as a concentration detection device. In this case, the infrared energy (the infrared light) emitted from the substance is dispersed by the variable wavelength interference filter and is then analyzed, and the concentration of the test object in a sample is measured.

As described above, the variable wavelength interference filter, the optical module, and the electronic apparatus can be applied to any device for dispersing predetermined light from the incident light. Further, since the variable wavelength interference filter can disperse the light having a plurality of wavelengths with a single device as described above, the measurement of the spectrum of a plurality of wavelengths and detection of a plurality of components can be performed with accuracy. Therefore, compared to the conventional device of taking out desired wavelengths with a plurality of devices, downsizing of the optical module and the electronic apparatus can be promoted, and the optical module and the electronic apparatus can preferably be used as, for example, the portable or in-car optical device.

Besides the above, specific structures to be adopted when putting the invention into practice can arbitrarily be replaced with other structures and so on within the range in which the advantages of the invention can be achieved.

The entire disclosure of Japanese Patent Application No. 2011-211497 filed Sep. 27, 2011 is expressly incorporated herein by reference.

What is claimed is:

1. An optical filter device comprising:
    an interference filter having:
        a first substrate,
        a second substrate opposed to the first substrate,
        a first reflecting film disposed on the first substrate and adapted to partially reflect and partially transmit light impinging on the first reflecting film, and
        a second reflecting film disposed on the second substrate, the second reflecting film being opposed to the first reflecting film across a gap, and being adapted to partially reflect and partially transmit light impinging on the second reflecting film; and
    a housing holding the interference filter,
    wherein the housing has a base substrate and a lid bonded to the base substrate,
    at least one of the base substrate and the lid is provided with a light passage hole in an area opposed to the first reflecting film and the second reflecting film,
    the housing has a light transmissive substrate covering the light passage hole,
    an edge of the light transmissive substrate is located outside an edge of the light passage hole in a plan view of the light transmissive substrate,
    the light transmissive substrate is bonded to the at least one of the base substrate and the lid provided with the light passage hole in an area between the edge of the light passage hole to the edge of the light transmissive substrate in the plan view, and
    in the plan view of the light transmissive substrate, denoting two intersections between a straight line connecting two points on an outer peripheral edge of the light passage hole and a substrate edge of the light transmissive substrate by substrate end points, a distance between the two points on the outer peripheral edge of the light passage hole by "d," and a distance between the substrate end points by "a," a relationship of a/d≥1.6 is fulfilled.

2. The optical filter device according to claim 1, wherein the lid includes:
    a lid bonding section bonded to the base substrate,
    a sidewall section continuous to the lid bonding section, and rising in a direction intersecting with the base substrate, and
    a top surface section opposed to the base substrate and continuous to the sidewall section.

3. The optical filter device according to claim 1, wherein the light transmissive substrate is bonded to an exterior surface of the one of the base substrate and the lid provided with the light passage hole, the exterior surface being opposite to the surface facing to the interference filter.

4. The optical filter device according to claim 3, wherein the light passage hole is provided to each of the base substrate and the lid, and the light transmissive substrate is provided to each of the two light passage holes.

5. The optical filter device according to claim 4, wherein a pressure inside the housing is lower than atmospheric pressure.

6. The optical filter device according to claim 5, wherein at least one hole penetrating through at least one of the base substrate and the lid and a seal member sealing the hole are provided to at least one of the base substrate and the lid.

7. The optical filter device according to claim 1, wherein the interference filter has an electrode section, and the base substrate has:
    an interior surface terminal section disposed on a lid-opposed surface opposed to the lid, and electrically connected to the electrode section, and
    an exterior surface terminal section disposed on a base exterior surface opposite to the lid-opposed surface, and electrically connected to the interior surface terminal section.

8. The optical filter device according to claim 7, wherein the base substrate has a through hole disposed from the lid-opposed surface to the base exterior surface, and a conductive member with which the through hole is filled, and
the interior surface terminal section and the exterior surface terminal section are electrically connected via the conductive member.

9. The optical filter device according to claim 1, wherein the interference filter has a non-light transmissive member having a ring shape disposed on a light entrance surface which the light having passed through the light passage hole enters.

10. An optical module comprising:
the optical filter device according to claim 1; and
a detection section adapted to detect the light emitted by the interference filter.

11. An electronic apparatus comprising:
the optical filter device according to claim 1.

12. An optical filter device comprising:
    an interference filter having:
        a first reflecting film adapted to partially reflect and partially transmit light impinging on the first reflecting film, and
        a second reflecting film opposed to the first reflecting film across a gap, the second reflecting film being adapted to partially reflect and partially transmit light impinging on the second reflecting film; and
    a housing holding the interference filter,
    wherein a light passage hole is provided in a part of the housing opposed to the first reflecting film and the second reflecting film,
    the housing has a light transmissive substrate covering the light passage hole,
    an edge of the light transmissive substrate overlaps a portion of the housing in a plan view of the light transmissive substrate, and the light transmissive substrate is bonded to the housing in a continuous area between an edge of the light passage hole and the edge of the light transmissive substrate, the continuous area surrounding the light passage hole, and
    in the plan view of the light transmissive substrate, denoting two intersections between a straight line connecting two points on an outer peripheral edge of the light passage hole and a substrate edge of the light transmissive substrate by substrate end points, a distance between the two points on the outer peripheral edge of the light passage hole by "d," and a distance between the substrate end points by "a," a relationship of a/d≥1.6 is fulfilled.

13. An optical filter device comprising:
an interference filter having:
   a first substrate,
   a second substrate opposed to the first substrate,
   a first reflecting film disposed on the first substrate and adapted to partially reflect and partially transmit light impinging on the first reflecting film, and
   a second reflecting film disposed on the second substrate, the second reflecting film being opposed to the first reflecting film across a gap and being adapted to partially reflect and partially transmit light impinging on the second reflecting film; and
a housing holding the interference filter,
wherein the housing has a base member having a light passage hole in an area opposed to the first reflecting film, and a lid bonded to the base member,
the base member has a light transmissive substrate covering the light passage hole,
an edge of the light transmissive substrate partially overlaps the base member in a plan view of the light transmissive substrate, the light transmissive substrate is bonded to the base member in a continuous area between an edge of the light passage hole and the edge of the light transmissive substrate, the continuous area surrounding the light passage hole, and
in the plan view of the light transmissive substrate, denoting two intersections between a straight line connecting two points on an outer peripheral edge of the light passage hole and a substrate edge of the light transmissive substrate by substrate end points, a distance between the two points on the outer peripheral edge of the light passage hole by "d," and a distance between the substrate end points by "a," a relationship of a/d≥1.6 is fulfilled.

14. An optical filter device comprising:
an interference filter having:
   a first substrate,
   a second substrate opposed to the first substrate,
   a first reflecting film disposed above the first substrate and adapted to partially reflect and partially transmit light impinging on the first reflecting film, and
   a second reflecting film disposed on the second substrate, the second reflecting film being opposed to the first reflecting film across a gap and being adapted to partially reflect and partially transmit light impinging on the second reflecting film; and
a housing holding the interference filter,
wherein the housing has a base member, a lid bonded to the base member, and a light passage hole in an area opposed to the second reflecting film,
the lid has a light transmissive substrate covering the light passage hole, and
an edge of the light transmissive substrate partially overlaps the lid in a plan view of the light transmissive substrate, the light transmissive substrate is bonded to the lid in a continuous area between an edge of the light passage hole and the edge of the light transmissive substrate, the continuous area surrounding the light passage hole, and in the plan view of the light transmissive substrate, denoting two intersections between a straight line connecting two points on an outer peripheral edge of the light passage hole and a substrate edge of the light transmissive substrate by substrate end points, a distance between the two points on the outer peripheral edge of the light passage hole by "d," and a distance between the substrate end points by "a," a relationship of a/d≥1.6 is fulfilled.

15. The optical filter device according to claim 14, wherein
the base member is provided with a hole penetrating the base member, and a seal member sealing the hole.

16. An optical filter device comprising:
an interference filter having:
   a first substrate,
   a second substrate opposed to the first substrate,
   a first reflecting film on the first substrate, and
   a second reflecting film on the second substrate and facing the first reflecting film across a gap;
a housing containing the interference filter, the housing including a light passage hole aligned with the first and second reflecting films; and
a light transmissive substrate hermetically bonded to an exterior surface of the housing so as to completely overlap the light passage hole,
wherein in a plan view of the light transmissive substrate, denoting two intersections between a straight line connecting two points on an outer peripheral edge of the light passage hole and a substrate edge of the light transmissive substrate by substrate end points, a distance between the two points on the outer peripheral edge of the light passage hole by "d," and a distance between the substrate end points by "a," a relationship of a/d≥1.6 is fulfilled.

17. The optical filter device according to claim 16, wherein the housing comprises:
a base substrate; and
a lid bonded to the base substrate,
wherein the lid includes:
   a lid bonding section bonded to the base substrate,
   a sidewall section continuous to the lid bonding section, and rising in a direction intersecting with the base substrate, and
   a top surface section opposed to the base substrate and continuous to the sidewall section; and
wherein the light passage hole is formed in one of the base substrate and the lid.

18. The optical filter device according to claim 17, further comprising:
a second light passage hole formed in the other of the base substrate and the lid; and
a second light transmissive substrate hermetically bonded to the other of the base substrate and the lid and completely so as to completely overlap the second light passage hole,
wherein the second plight passage hole is aligned with the first and second reflecting films.

* * * * *